US008691196B2

(12) United States Patent
Genain et al.

(10) Patent No.: US 8,691,196 B2
(45) Date of Patent: Apr. 8, 2014

(54) PHOTOPROTECTIVE TREATMENT OF KERATIN FIBERS BY APPLICATION OF HEAT

(75) Inventors: Gilles Genain, Paris (FR); Boris Lalleman, Paris (FR)

(73) Assignee: L'Oreal, Paris (FR)

( * ) Notice: Subject to any disclaimer, the term of this patent is extended or adjusted under 35 U.S.C. 154(b) by 1985 days.

(21) Appl. No.: 11/476,076

(22) Filed: Jun. 28, 2006

(65) Prior Publication Data

US 2007/0056121 A1    Mar. 15, 2007

Related U.S. Application Data

(60) Provisional application No. 60/697,968, filed on Jul. 12, 2005.

(30) Foreign Application Priority Data

Jun. 28, 2005 (FR) ...................... 05 51794

(51) Int. Cl.
*A61Q 5/00* (2006.01)

(52) U.S. Cl.
USPC ..................... 424/70.1; 132/202; 132/208

(58) Field of Classification Search
None
See application file for complete search history.

(56) References Cited

U.S. PATENT DOCUMENTS

| | | | |
|---|---|---|---|
| 4,592,908 A * | 6/1986 | Wajaroff et al. | 424/70.2 |
| 5,045,307 A * | 9/1991 | Marschner et al. | 424/59 |
| 6,211,125 B1 | 4/2001 | Crudele et al. | |
| 6,740,317 B1 | 5/2004 | Cho et al. | |
| 6,824,764 B2 * | 11/2004 | Devin-Baudoin et al. | 424/70.1 |
| 6,824,765 B2 * | 11/2004 | Gawtrey et al. | 424/70.1 |
| 7,608,115 B2 * | 10/2009 | De La Mettrie | 8/405 |
| 2002/0139384 A1 | 10/2002 | Kamis et al. | |
| 2005/0013786 A1 | 1/2005 | Sabbagh et al. | |
| 2005/0196369 A1 * | 9/2005 | Ueyama et al. | 424/70.2 |

FOREIGN PATENT DOCUMENTS

| | | | |
|---|---|---|---|
| DE | 100 51 773 | A1 | 4/2002 |
| EP | 0 437 006 | B1 | 7/1991 |
| EP | 0 981 318 | A1 | 3/2000 |
| EP | 1 118 319 | A1 | 7/2001 |
| EP | 1 468 667 | A1 | 10/2004 |
| EP | 1 568 350 | A2 | 8/2005 |
| FR | 2831810 | * | 5/2003 |
| FR | 2831812 | * | 5/2003 |
| JP | H03-148211 | A | 6/1991 |
| JP | H04-210906 | A | 8/1992 |
| JP | H05-043437 | A | 2/1993 |
| JP | H07-187961 | A | 7/1995 |
| JP | 2001-213741 | A | 8/2001 |
| JP | 2002-017427 | A | 1/2002 |
| JP | 2002-338440 | A | 11/2002 |
| JP | 2004-189727 | A | 7/2004 |
| JP | 2004-217672 | A | 8/2004 |
| JP | 2004-262906 | A | 9/2004 |
| JP | 2005-145978 | A | 6/2005 |
| WO | WO 98/51265 | A1 | 11/1998 |
| WO | WO 2004/047777 | A1 | 6/2004 |
| WO | WO 2004/098550 | * | 11/2004 |
| WO | WO 2004/098550 | A1 | 11/2004 |

OTHER PUBLICATIONS

Anonymous, "The use of UV filters in cosmetic and pharmaceutical sunscreen formulations", IP Com Journal, 2002, pp. 1-35, New York, USA.
European Search Report corresponding to EP 06 11 5282, issued on Oct. 19, 2006, 5 pages.
English translation of Notice of Reasons for Rejection issued on Nov. 1, 2011, in Japanese Patent Application No. 2006-177274.
English translation of Decision of Rejection issued on Feb. 5, 2013, in Japanese Patent Application No. 2006-177274.

* cited by examiner

*Primary Examiner* — Jyothsna Venkat
(74) *Attorney, Agent, or Firm* — Buchanan Ingersoll & Rooney PC

(57) ABSTRACT

Keratin fibers, in particular human hair and especially artificially dyed human hair, are protected against the action of atmospheric agents and especially against the action of light by application to the keratin fibers/hair of a composition containing at least one protective agent having a log P of less than or equal to 6, followed by the application to the fibers hair of a heating iron at a temperature of greater than or equal to 60° C.

27 Claims, No Drawings

PHOTOPROTECTIVE TREATMENT OF KERATIN FIBERS BY APPLICATION OF HEAT

CROSS-REFERENCE TO PRIORITY/PROVISIONAL APPLICATIONS

This application claims priority under 35 U.S.C. §119 of FR 05/51794, filed Jun. 28, 2005, and of U.S. Provisional Application No. 60/697,968, filed Jul. 12, 2005, each hereby expressly incorporated by reference and each assigned to the assignee hereof.

BACKGROUND OF THE INVENTION

1. Technical Field of the Invention

The present invention relates to a process for treating keratin fibers which comprises the application to the keratin fibers, in particular human hair, of a composition comprising at least one protective agent with a log P of less than or equal to 6, followed by the application to the fibers of a heating iron or element at a temperature of greater than or equal to 60° C.

The present invention also relates to the use of the said process for protecting keratin fibers, in particular human hair, against the effects of UV radiation and more especially for protecting artificially dyed hair.

2. Description of Background and/or Related and/or Prior Art

It is well known that the hair is sensitized or embrittled to varying degrees by the action of atmospheric agents and especially the light. Many publications disclose that natural light destroys certain amino acids of the hair. These attacking factors impair the hair fiber and reduce its mechanical properties, for instance the tensile strength, the breaking load and the elasticity, or its resistance to swelling in an aqueous medium. The hair is then dull, coarse and brittle.

It is also known that light especially has a tendency to attack the natural color of the hair, and also the artificial color of dyed hair. The color of the hair gradually fades or turns to relatively unattractive or undesirable shades.

The effect of light is even more visible on hair dyed by artificial coloration, in particular oxidation dyeing or direct dyeing. In this case, exposure to light leads to degradation of the dyes present both in the hair and on its surface. This results in substantial fading and/or changing of the color of the hair.

Substances for protecting the hair against the degradation caused by atmospheric attacking factors, such as light, have been sought for many years in the cosmetics industry. Products that protect the integrity of keratin fibers, i.e., their composition, their surface condition, their natural or artificial color and their intrinsic mechanical properties (the tensile strength, breaking load and elasticity, or their resistance to swelling in an aqueous medium) are sought in particular.

To combat these types of degradation of hair keratin, it has already been proposed to use protecting agents such as organic UV-screening agents, antioxidants, chelating agents or free-radical scavengers.

Certain substances capable of screening out light radiation, for instance 2-hydroxy-4-methoxybenzophenone-5-sulfonic acid or salts thereof (FR-A-2,627,085), 4-(2-oxo-3-bornylidenemethyl)benzenesulfonic acid or salts thereof (EP-A-329,032) or lactoferrin (FR-A-2,673,839) have thus been proposed.

JP 05-043437 discloses dye compositions containing 2-hydroxy-4-methoxybenzophenone-5-sulfonic acid or salts thereof, an aromatic alcohol and an acidic direct dye.

However, the current cosmetic compositions containing protecting agents are not entirely satisfactory, in particular on hair dyed with blue oxidation dyes, for instance those obtained with couplings comprising meta-phenylenediamines.

SUMMARY OF THE INVENTION

A novel process for treating keratin fibers, in particular human hair, has now surprisingly been discovered, comprising the application to the said keratin fibers of a composition which comprises at least one protective agent with a log P of less than or equal to 6, followed by the application to the fibers of a heating element or iron at a temperature of greater than or equal to 60° C. This process affords better protection of the said fibers against the action of atmospheric agents and especially against the harmful effects of light.

An improvement in the light-fastness of the coloration of hair dyed by direct dyeing or by oxidation dyeing is in particular obtained by means of this process. The treatment process according to the invention can also provide a light-protective effect that withstands shampooing.

All these form the basis of the present invention. Thus, according to the present invention, a process is featured for treating keratin fibers, in particular human hair, comprising applying to the said keratin fibers a composition containing, in a physiologically acceptable medium, at least one protective agent with a log P of less than or equal to 6, followed by applying to the fibers a heating iron at a temperature of greater than or equal to 60° C.

The present invention also features the use of the said process for protecting keratin fibers against the action of atmospheric agents and especially against the action of light.

The present invention also features the use of the said process as a post-treatment to oxidation dyeing or direct dyeing of keratin fibers and more particularly of the hair.

The present invention also features a process for dyeing keratin fibers, in particular human hair, comprising at least steps a), b) and c) below:

a) direct dyeing or oxidation dyeing of the said fibers is performed,
b) a composition comprising, in a physiologically acceptable medium and in particular a cosmetically acceptable medium, at least one protective agent with a log P of less than or equal to 6, is applied to the said fibers
c) a heating iron at a temperature of greater than or equal to 60° C. is applied to the said fibers; the order of steps a) and b) being irrelevant and step c) being performed after step a) or step b) on condition that step b) has already been performed.

The various aspects of the invention will now be detailed. All of the meanings and definitions of the compounds used in the present invention given below are valid for all of the aspects of the invention.

DETAILED DESCRIPTION OF BEST MODE AND SPECIFIC/PREFERRED EMBODIMENTS OF THE INVENTION

In the context of the invention, the log P value conventionally is the partition coefficient of the dye from octanol and water. The log P value may be calculated according to the method described in the article by Meylan and Howard "Atom/Fragment contribution method for estimating octanol-water partition coefficient", *J. Pharm. Sci.*, 84: 83-92, 1995. This value may also be calculated by means of numerous software packages available on the market, which determine the log P value as a function of the structure of a molecule. By way of example, the Epiwin software from the United States Environmental Agency and the Virtual Computational Chemistry Laboratory software may be mentioned.

The heating iron that is useful in the context of the invention is a heating iron conventionally used in the field of haircare. Such an iron, for example a crimping iron or a smoothing iron, is well known in the field of hair treatment. For example, irons that are useful for implementation of the present invention are flat or round irons described in U.S. Pat. Nos. 4,103,145, 4,308,878, 5,983,903, 5,957,140 and 5,494,058.

In the context of the invention, the temperature is greater than or equal to 60° C. This temperature preferably ranges from 60° C. to 220° C. This temperature more preferentially ranges from 60° C. to 120° C.

The iron may be applied by successive separate touches of a few seconds, or by gradually moving or sliding along the locks.

It is possible, from the application of the composition containing the protective agent and the application of the heating iron to the keratin fibers, to envisage a pause.

The said pause will preferably range from 30 seconds to 60 minutes and more preferentially from 1 to 30 minutes.

It is also possible to carry out a rinsing step and/or a step of washing with shampoo before or after applying the composition containing the protective agent(s) and optionally after applying the iron.

The process according to the invention may include an additional step of total or partial drying of the keratin fibers with a hairdryer before using the iron, so as to avoid substantial evolution of steam that might burn the hands of the hair stylist and the scalp of the model.

The keratin fiber protective agent may be any active agent that is useful for preventing or limiting the degradation of keratin fibers, in particular of the hair, caused by atmospheric attacking factors and more particularly light.

Thus, the keratin fiber protective agent may be selected from organic UV-screening agents, free-radical scavengers and antioxidants.

The term "free-radical scavenger" means any compound capable of trapping free radicals.

The organic UV-screening agents (systems for screening out UV radiation) are selected from water-soluble or liposoluble screening agents with a log P of less than or equal to 6.

The organic screening agents are selected especially from dibenzoylmethane derivatives; anthranilates; cinnamic derivatives; salicylic derivatives; camphor derivatives; benzophenone derivatives; β,β-diphenylacrylate derivatives; benzotriazole derivatives; triazine derivatives; benzalmalonate derivatives; benzimidazole derivatives; imidazolines; bis-benzolyl derivatives as described in EP-669,323 and U.S. Pat. No. 2,463,264; p-aminobenzoic acid (PABA) derivatives; benzoxazole derivatives as described in EP-0-832,642, EP-1-027,883, EP-1-300,137 and DE-101,62,844; dimers derived from α-alkylstyrene, such as those described in DE-198,55,649; 4,4-diarylbutadienes such as those described in EP-0-967,200, DE-197.46,654, DE-197,55,649, EP-A-1,008,586, EP-1-133,980 and EP-133,981, and mixtures thereof.

As examples of organic UV-screening agents, representative are those denoted hereinbelow under their INCI name:

para-Aminobenzoic Acid Derivatives:
PABA,
Ethyl PABA,
Ethyl dihydroxypropyl PABA,
Ethylhexyl dimethyl PABA marketed in particular under the name "Escalol 507" by ISP,
Glyceryl PABA,
PEG-25 PABA marketed under the name "Uvinul P25" by BASF.

Cinnamic Derivatives:
Ethylhexyl methoxycinnamate marketed in particular under the trademark "Parsol MCX" by Hoffmann LaRoche,
Isopropyl methoxycinnamate,
Isoamyl methoxycinnamate marketed under the trademark "Neo Heliopan E 1000" by Haarmann and Reimer,
Cinoxate,
DEA methoxycinnamate,
Diisopropyl methylcinnamate.

Dibenzoylmethane Derivatives:
Butylmethoxydibenzoylmethane marketed especially under the trademark "Parsol 1789" by Hoffmann LaRoche,
Isopropyldibenzoylmethane marketed especially under the trademark "Eusolex 8020" by Merck.

Salicylic Derivatives:
Ethylhexyl salicylate marketed under the name "Neo Heliopan OS" by Haarmann and Reimer,
Dipropylene glycol salicylate marketed under the name "Dipsal" by Scher,
TEA salicylate marketed under the name "Neo Heliopan TS" by Haarmann and Reimer.

β,β-Diphenylacrylate Derivatives:
Etocrylene marketed in particular under the trademark "Uvinul N35" by BASF.

Benzophenone Derivatives:
Benzophenone-1 marketed under the trademark "Uvinul 400" by BASF,
Benzophenone-2 marketed under the trademark "Uvinul D50" by BASF,
Benzophenone-3 or Oxybenzone marketed under the trademark "Uvinul M40" by BASF,
Benzophenone-4 marketed under the trademark "Uvinul MS40" by BASF, Benzophenone-5,
Benzophenone-6 marketed under the trademark "Helisorb 11" by Norquay,
Benzophenone-8 marketed under the trademark "SpectraSorb UV-24" by American Cyanamid,
Benzophenone-9 marketed under the trademark "Uvinul DS-49" by BASF.

Benzylidenecamphor Derivatives:
3-Benzylidenecamphor manufactured under the name "Mexoryl SD" by Chimex,
4-Methylbenzylidenecamphor marketed under the name "Eusolex 6300" by Merck,
Benzylidenecamphorsulfonic acid manufactured under the name "Mexoryl SL" by Chimex,
Camphor benzalkonium methosulfate manufactured under the name "Mexoryl SO" by Chimex,
Terephthalylidenedicamphorsulfonic acid manufactured under the name "Mexoryl SX" by Chimex.

Phenylbenzimidazole Derivatives:
Phenylbenzimidazolesulfonic acid marketed in particular under the trademark "Eusolex 232" by Merck,
Disodium phenyidibenzimidazoletetrasulfonate marketed under the trademark "Neo Heliopan AP" by Haarmann and Reimer.

Imidazoline Derivatives:
Ethylhexyldimethoxybenzylidenedioxoimidazoline propionate.

As liposoluble (or lipophilic) organic UV-screening agents that are suitable for use in the present invention, more particularly exemplary are:

Ethylhexyl methoxycinnamate,
Butylmethoxydibenzoylmethane,
Ethylhexyl salicylate,
Benzophenone-3,
4-Methylbenzylidenecamphor, The free-radical scavengers that may be used in the composition according to the invention comprise vitamin E and derivatives thereof such as tocopheryl acetate; bioflavonoids; certain enzymes, for instance catalase, superoxide dismutase and wheatgerm extracts containing it, lactoperoxidase, glutathione peroxidase and quinone reductases; benzylcyclanones; substituted naphthalenones; pidolates; guanosine; lignans; and melatonin.

The antioxidants are especially selected from phenols such as BHA (tert-butyl-4-hydroxyanisole), BHT (2,6-di-tert-butyl-p-cresol), TBHQ (tert-butylhydroquinone), polyphenols such as proanthocyanidol oligomers and flavonoids, hindered amines known under the generic term HALS (Hindered Amine Light Stabilizer) such as tetraaminopiperidine, erythorbic acid, polyamines such as spermine, superoxide dismutase or lactoferrin.

The keratin fiber protective agents will be selected more particularly from organic UV-screening agents.

According to the invention, the keratin fiber protective agent(s) will preferably be present in concentrations ranging from 0.15% to 50% by weight, preferably from 0.35% to 30% by weight and more particularly from 0.5% to 20% by weight relative to the total weight of the composition.

According to one preferred embodiment of the invention, protective agents with a log P (octanol/water partition coefficient) of less than 4.5 and more preferentially less than 2 will be used.

According to one particularly preferred embodiment of the invention, protective agents that are soluble in the aqueous medium of the composition will be used, in particular protective agents that are soluble at 25° C. and to at least 0.5% in water or $C_1$-$C_4$ lower alcohols, for instance ethanol. More particularly, water-soluble organic UV-screening agents will be used, selected from:
PABA,
PEG-25 PABA,
Benzylidenecamphorsulfonic acid,
Camphorbenzalkonium methosulfate,
Terephthalylidenedicamphorsulfonic acid,
Phenylbenzimidazolesulfonic acid,
Disodium phenyldibenzimidazoletetrasulfonate,
Benzophenone-4,
Benzophenone-5,
Benzophenone-9,
or mixtures thereof.

Among these screening agents, Benzophenone-4 will be used more particularly.

The physiologically acceptable and in particular cosmetically acceptable medium preferably consists of water or of a mixture of water and of at least one cosmetically acceptable organic solvent. Examples of organic solvents that may be mentioned include $C_1$-$C_4$ lower alkanols such as ethanol and isopropanol; polyols and polyol ethers, for instance 2-butoxyethanol, propylene glycol, propylene glycol monomethyl ether and diethylene glycol monomethyl ether and monoethyl ether, and mixtures thereof.

The solvents are preferably present in proportions preferably of from 1% to 40% by weight approximately and even more preferentially from 3% to 30% by weight approximately relative to the total weight of the dye composition.

The compositions according to the invention containing the protective agent(s) may also contain various adjuvants conventionally used in hair treatment compositions, such as anionic, cationic, nonionic, amphoteric or zwitterionic surfactants or mixtures thereof, anionic, cationic, nonionic, amphoteric or zwitterionic polymers or mixtures thereof, mineral or organic thickeners, and in particular anionic, cationic, nonionic and amphoteric polymeric associative thickeners, penetrants, sequestrants, fragrances, buffers, dispersants, conditioning agents, for instance volatile or nonvolatile, modified or unmodified silicones, film-forming agents, ceramides, preservatives and opacifiers.

According to one preferred embodiment of the invention, the hair compositions according to the invention containing the protective agent(s) also comprise at least one aromatic alcohol and at least one aromatic carboxylic acid.

The term "aromatic alcohol" means any compound that is liquid at room temperature and atmospheric pressure, comprising at least one benzene or naphthalene ring and at least one alcohol function (OH) directly linked to the ring or linked to at least one substituent of the said ring. The alcohol function will preferably be on a substituent of the benzene or naphthalene ring.

Among the aromatic alcohols that may be used in the composition according to the invention, mention may be made in particular of:
benzyl alcohol
benzoylisopropanol
benzyl glycol
phenoxyethanol
dichlorobenzyl alcohol
methylphenylbutanol
phenoxyisopropanol
phenylisohexanol
phenylpropanol
phenylethyl alcohol
mixtures thereof.

Benzyl alcohol will be selected more particularly.

According to the invention, the aromatic alcohol(s) may represent from 0.01% to 50% by weight, preferably from 0.1% to 30% by weight and more particularly from 1% to 20% by weight relative to the total weight of the composition. Preferably, they will be used in concentrations of greater than 1% by weight.

The hair compositions according to the invention also comprise at least one optionally salified aromatic carboxylic acid.

The term "aromatic carboxylic acid" means any compound comprising at least one benzene or naphthalene ring and at least one carboxylic acid function (COOH), in free or salified form, directly linked to the ring or linked to at least one substituent of the said ring. Preferably, the acid function will be directly linked to the benzene or naphthalene ring.

The aromatic carboxylic acid salts may be selected especially from alkali metal (sodium or potassium) or alkaline-earth metal (calcium or magnesium) salts or organic amine or ammonium salts.

Among the aromatic carboxylic acids that may be used in the compositions according to the invention, mention may be made in particular of:
benzoic acid
para-anisic acid
diphenolic acid
ferulic acid
hippuric acid
3-hydroxybenzoic acid
4-hydroxybenzoic acid
phenylthioglycolic acid
acetylsalicylic acid para-, meta- or ortho-phthalic acid, and also the salified forms thereof, and mixtures thereof.

Benzoic acid will be selected more particularly.

According to the invention, the aromatic acid(s) or salts thereof may represent from 0.001% to 30% by weight, preferably from 0.01% to 20% by weight and more particularly from 0.1% to 10% by weight relative to the total weight of the composition.

The compositions according to the invention may also contain one or more conditioning agents.

In the context of the present patent application, the term "conditioning agent" means any agent whose function is to improve the cosmetic properties of the hair, in particular the softness, disentangling, feel, smoothness and static electricity.

The conditioning agents may be in liquid, semi-solid or solid form such as, for example, oils, waxes or gums.

According to the invention, the conditioning agents may be selected from synthetic oils such as polyolefins, plant oils, fluoro oils or perfluoro oils, natural or synthetic waxes, silicones, non-polysaccharide cationic polymers, compounds of ceramide type, cationic surfactants, fatty amines, fatty acids and derivatives thereof, and also mixtures of these various compounds.

The synthetic oils are especially polyolefins, in particular poly-α-olefins and more particularly:

of hydrogenated or non-hydrogenated polybutene type, and preferably hydrogenated or non-hydrogenated polyisobutene type.

Isobutylene oligomers with a molecular weight of less than 1,000 and mixtures thereof with polyisobutylenes with a molecular weight of greater than 1,000, and preferably from 1,000 and 15,000, are preferably used.

As examples of poly-α-olefins that can be used in the context of the present invention, mention may be made more particularly of the polyisobutenes marketed under the name Permethyl 99 A, 101 A, 102 A, 104 A (n=16) and 106 A (n=38) by Presperse Inc., or, alternatively, the products marketed under the name Arlamol HD (n=3) by ICI (n denoting the degree of polymerization), of hydrogenated or non-hydrogenated polydecene type.

Such products are marketed, for example, under the names Ethylflo by Ethyl Corp. and Arlamol PAO by ICI.

The animal or plant oils are preferably selected from the group formed by sunflower oil, corn oil, soybean oil, avocado oil, jojoba oil, marrow oil, grapeseed oil, sesame oil, hazelnut oil, fish oils, glyceryl tricaprocaprylate, or plant or animal oils of formula $R_9COOR_{10}$ in which $R_9$ is a higher fatty acid residue containing from 7 to 29 carbon atoms and $R_{10}$ is a linear or branched hydrocarbon-based chain containing from 3 to 30 carbon atoms, in particular alkyl or alkenyl, for example purcellin oil or liquid jojoba wax.

It is also possible to use natural or synthetic essential oils such as, for example, eucalyptus oil, lavendin oil, lavender oil, vetiver oil, Litsea cubeba oil, lemon oil, sandalwood oil, rosemary oil, camomile oil, savory oil, nutmeg oil, cinnamon oil, hyssop oil, caraway oil, orange oil, geraniol oil, cade oil and bergamot oil.

The waxes are natural (animal or plant) or synthetic substances that are solid at room temperature (20°-25° C.). They are insoluble in water, soluble in oils and are capable of forming a water-repellent film.

For the definition of waxes, mention may be made, for example, of P. D. Dorgan, *Drug and Cosmetic Industry*, December 1983, pp. 30-33.

The wax(es) is (are) selected in particular from carnauba wax, candelilla wax, alfalfa wax, paraffin wax, ozokerite, plant waxes such as olive tree wax, rice wax, hydrogenated jojoba wax or the absolute waxes of flowers such as the essential wax of blackcurrant flower marketed by Bertin (France), animal waxes such as beeswaxes, or modified beeswaxes (cerabellina); other waxes or waxy starting materials which can be used according to the invention are, in particular, marine waxes such as the product marketed by Sophim under the reference M82, and polyethylene waxes or polyolefin waxes in general.

The conditioning agents that are preferred according to the invention are cationic polymers and silicones.

The non-saccharide cationic polymers that may be used in accordance with the present invention may be selected from all those already known per se as improving the cosmetic properties of hair treated with detergent compositions, i.e., especially those described in EP-A-0-337,354 and in FR-A-2,270,846, FR-2,383,660, FR-2,598,611, FR-2,470,596 and FR-2,519,863.

The term "non-saccharide polymers" is understood to mean polymers that do not contain a glycoside bond from monosaccharides.

Even more generally, for the purpose of the present invention, the term "cationic polymer" is any polymer containing cationic groups and/or groups that may be ionized into cationic groups.

The cationic polymers that are preferred are selected from those containing units comprising primary, secondary, tertiary and/or quaternary amine groups that either may form part of the main polymer chain or may be borne by a side substituent directly attached thereto.

The cationic polymers used generally have a number-average molecular mass of from 500 and $5 \times 10^6$ approximately and preferably from $10^3$ and $3 \times 10^6$ approximately.

Among the cationic polymers that may be mentioned more particularly are polymers of the polyamine, polyamino amide and polyquaternary ammonium type. These are known products.

The polymers of the polyamine, polyamino amide and polyquaternary ammonium type that may be used in accordance with the present invention, and that may especially be mentioned, are those described in FR-2,505,348 and FR-2,542,997. Among these polymers, mention may be made of:

(1) homopolymers or copolymers derived from acrylic or methacrylic esters or amides and comprising at least one of the units of the following formulae:

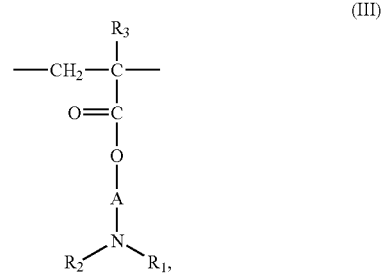

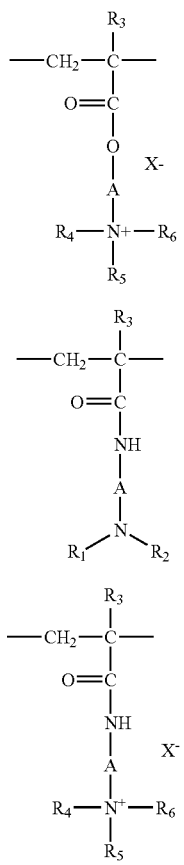

in which:
R₁ and R₂, which may be identical or different, are each hydrogen or an alkyl radical having from 1 to 6 carbon atoms, and preferably methyl or ethyl;
R₃, which may be identical or different, is a hydrogen atom or a CH₃ radical;
A, which may be identical or different, is a linear or branched alkyl radical having 1 to 6 carbon atoms, preferably 2 or 3 carbon atoms, or a hydroxyalkyl radical having 1 to 4 carbon atoms;
R₄, R₅ and R₆, which may be identical or different, are each an alkyl radical having from 1 to 18 carbon atoms or a benzyl radical and preferably an alkyl radical having from 1 to 6 carbon atoms;
X is an anion derived from a mineral or organic acid, such as a methosulfate anion or a halide such as chloride or bromide.

The copolymers of family (1) can also contain one or more structural units derived from comonomers which may be selected from the family of acrylamides, methacrylamides, diacetone acrylamides, acrylamides and methacrylamides substituted on the nitrogen with lower (C₁-C₄) alkyls, acrylic or methacrylic acids or esters thereof, vinyllactams such as vinylpyrrolidone or vinylcaprolactam, and vinyl esters.

Thus, among these copolymers of family (1), mention may be made of:
copolymers of acrylamide and of dimethylaminoethyl methacrylate quaternized with dimethyl sulfate or with a dimethyl halide, such as the product marketed under the name Hercofloc by Hercules,
the copolymers of acrylamide and of methacryloyloxyethyltrimethylammonium chloride described, for example, in EP-A-080,976 and marketed under the name Bina Quat P 100 by Ciba Geigy,
the copolymer of acrylamide and of methacryloyloxyethyltrimethylammonium methosulfate marketed under the name Reten by Hercules,
quaternized or non-quaternized vinylpyrrolidone/dialkylaminoalkyl acrylate or methacrylate copolymers, such as the products marketed under the name Gafquat by ISP, such as, for example, Gafquat 734 or Gafquat 755, or, alternatively, the products known as Copolymer 845, 958 and 937. These polymers are described in detail in FR-2,077,143 and FR-2,393,573,
dimethylaminoethyl methacrylate/vinylcaprolactam/vinylpyrrolidone terpolymers, such as the product marketed under the name Gaffix VC 713 by ISP,
vinylpyrrolidone/methacrylamidopropyldimethylamine copolymers marketed in particular under the name Styleze CC 10 by ISP, and
quaternized vinylpyrrolidone/dimethylaminopropylmethacrylamide copolymers, such as the product marketed under the name Gafquat HS 100 by ISP.

(2) Polymers consisting of piperazinyl units and of divalent alkylene or hydroxyalkylene radicals containing straight or branched chains, optionally interrupted by oxygen, sulfur or nitrogen atoms or by aromatic or heterocyclic rings, as well as the oxidation and/or quaternization products of these polymers. Such polymers are described, in particular, in FR-2,162,025 and FR-2,280,361.

(3) Water-soluble polyamino-amides prepared in particular by polycondensation of an acidic compound with a polyamine; these polyamino amides can be crosslinked with an epihalohydrin, a diepoxide, a dianhydride, an unsaturated dianhydride, a bis-unsaturated derivative, a bis-halohydrin, a bis-azetidinium, a bis-haloacyldiamine, a bis-alkyl halide or, alternatively, with an oligomer resulting from the reaction of a difunctional compound which is reactive with a bis-halohydrin, a bis-azetidinium, a bis-haloacyldiamine, a bis-alkyl halide, an epihalohydrin, a diepoxide or a bis-unsaturated derivative; the crosslinking agent being used in proportions ranging from 0.025 to 0.35 mol per amine group of the polyamino amide; these polyamino amides can be alkylated or, if they contain one or more tertiary amine functions, they can be quaternized. Such polymers are described, in particular, in FR-2,252,840 and FR-2,368,508.

(4) The polyamino amide derivatives resulting from the condensation of polyalkylene polyamines with polycarboxylic acids followed by alkylation with difunctional agents. Mention may be made, for example, of adipic acid/dialkylaminohydroxyalkyldialkylenetriamine polymers in which the alkyl radical contains from 1 to 4 carbon atoms and preferably is methyl, ethyl or propyl. Such polymers are described in particular in FR-1,583,363.

Among these derivatives, mention may be made more particularly of the adipic acid/dimethylaminohydroxypropyl/diethylenetriamine polymers marketed under the name Cartaretine F, F4 or F8 by Sandoz.

(5) The polymers obtained by reaction of a polyalkylene polyamine containing two primary amine groups and at least one secondary amine group with a dicarboxylic acid selected from diglycolic acid and saturated aliphatic dicarboxylic acids having from 3 to 8 carbon atoms. The molar ratio from the polyalkylene polyamine and the dicarboxylic acid is from 0.8:1 and 1.4:1; the polyamino amide resulting therefrom being reacted with epichlorohydrin in a molar ratio of epichlorohydrin relative to the secondary amine group of the polyamino amide of from 0.5:1 and 1.8:1. Such polymers are described in particular in U.S. Pat. Nos. 3,227,615 and 2,961,347.

Polymers of this type are marketed in particular under the name Hercoseft 57 by Hercules Inc. or, alternatively, under the name PD 170 or Delsette 101 by Hercules in the case of the adipic acid/epoxypropyl/diethylenetriamine copolymer.

(6) Cyclopolymers of alkyldiallylamine or of dialkyldiallylammonium, such as the homopolymers or copolymers containing, as main constituent of the chain, units corresponding to formula (VII) or (VIII):

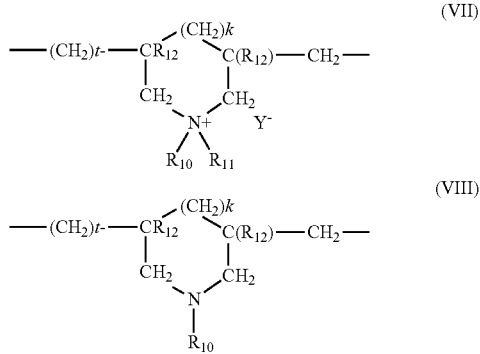

in which formulae k and t are equal to 0 or 1, the sum k+t being equal to 1; $R_{12}$ is a hydrogen atom or a methyl radical; $R_{10}$ and $R_{11}$, independently of each other, are each an alkyl radical having from 1 to 6 carbon atoms, a hydroxyalkyl radical in which the alkyl moiety preferably has 1 to 5 carbon atoms, a lower ($C_1$-$C_4$) amidoalkyl group, or $R_{10}$ and $R_{11}$ can is, together with the nitrogen atom to which they are attached, heterocyclic groups such as piperidyl or morpholinyl; $Y^-$ is an anion such as bromide, chloride, acetate, borate, citrate, tartrate, bisulfate, bisulfite, sulfate or phosphate. These polymers are described in particular in FR-2,080,759 and in its Certificate of Addition FR-2,190,406.

$R_{10}$ and $R_{11}$, independently of each other, preferably are each an alkyl radical containing from 1 to 4 carbon atoms.

Among the polymers defined above, mention may be made more particularly of the dimethyldiallylammonium chloride homopolymer marketed under the name Merquat 100 by Nalco (and its homologues of low weight-average molecular mass) and the copolymers of diallyldimethylammonium chloride and of acrylamide, marketed under the name Merquat 550.

(7) The quaternary diammonium polymer containing repeating units corresponding to the formula:

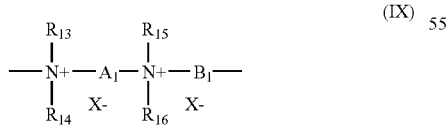

in which formula (IX):
$R_{13}$, $R_{14}$, $R_{15}$ and $R_{16}$, which may be identical or different, represent aliphatic, alicyclic or arylaliphatic radicals containing from 1 to 20 carbon atoms or lower hydroxyalkylaliphatic radicals, or, alternatively, $R_{13}$, $R_{14}$, $R_{15}$ and $R_{16}$, together or separately, constitute, with the nitrogen atoms to which they are attached, heterocycles optionally containing a second heteroatom other than nitrogen, or, alternatively, $R_{13}$, $R_{14}$, $R_{15}$ and $R_{16}$ represent a linear or branched $C_1$-$C_6$ alkyl radical substituted with a nitrile, ester, acyl or amide group or a group —CO—O—$R_{17}$-D or —CO—NH—$R_{17}$-D where $R_{17}$ is an alkylene and D is a quaternary ammonium group;

$A_1$ and $B_1$ represent polymethylene groups containing from 2 to 20 carbon atoms which may be linear or branched, saturated or unsaturated, and which may contain, linked to or intercalated in the main chain, one or more aromatic rings or one or more oxygen or sulfur atoms or sulfoxide, sulfone, disulfide, amino, alkylamino, hydroxyl, quaternary ammonium, ureido, amide or ester groups, and $X^-$ is an anion derived from a mineral or organic acid;

$A_1$, $R_{13}$ and $R_{15}$ can form, with the two nitrogen atoms to which they are attached, a piperazine ring; in addition, if $A_1$ is a linear or branched, saturated or unsaturated alkylene or hydroxyalkylene radical, $B_1$ can also is a group $(CH_2)_n$—CO-D-OC—$(CH_2)_n$—, n being an integer ranging from about 2 to 20, in which D is:

a) a glycol residue of formula: —O—Z—O—, where Z is a linear or branched hydrocarbon-based radical or a group corresponding to one of the following formulae:
—$(CH_2$—$CH_2$—$O)_x$—$CH_2$—$CH_2$—
—$[CH_2$—$CH(CH_3)$—$O]_y$—$CH_2$—$CH(CH_3)$—
where x and y is an integer from 1 to 4, representing a defined and unique degree of polymerization or any number from 1 to 4 representing an average degree of polymerization;

b) a bis-secondary diamine residue such as a piperazine derivative;

c) a bis-primary diamine residue of formula: —NH—Y—NH—, where Y is a linear or branched hydrocarbon-based radical, or, alternatively, the divalent radical —$CH_2$—$CH_2$—S—S—$CH_2$—$CH_2$—;

d) a ureylene group of formula: —NH—CO—NH—.

Preferably, $X^-$ is an anion such as chloride or bromide.

These polymers generally have a number-average molecular mass of from 1,000 and 100,000.

Polymers of this type are described in particular in the following French patents 2,320,330, 2,270,846, 2,316,271, 2,336,434 and 2,413,907 and U.S. Pat. Nos. 2,273,780, 2,375, 853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020.

It is more particularly possible to use polymers that consist of repeating units corresponding to the formula:

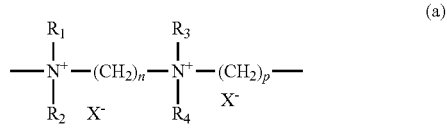

in which $R_1$, $R_2$, $R_3$ and $R_4$, which may be identical or different, is an alkyl or hydroxyalkyl radical containing from 1 to 4 carbon atoms approximately, n and p are integers ranging from 2 to 20 approximately, and $X^-$ is an anion derived from a mineral or organic acid.

A compound of formula (a) that is particularly preferred is the compound for which $R_1$, $R_2$, $R_3$ and $R_4$ represent a methyl radical and n=3, p=6 and X=Cl, referred to as hexadimethrine chloride according to the INCI nomenclature (CTFA).

(8) Polyquaternary ammonium polymers consisting of units of formula (X):

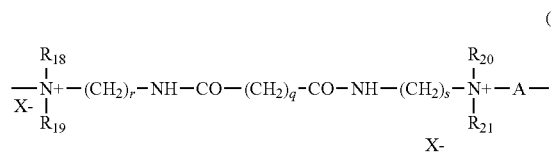

in which formula:
R$_{18}$, R$_{19}$, R$_{20}$ and R$_{21}$, which may be identical or different, represent a hydrogen atom or a methyl, ethyl, propyl, β-hydroxyethyl, β-hydroxypropyl or —CH$_2$CH$_2$(OCH$_2$CH$_2$)$_p$ OH radical,
where p is equal to 0 or to an integer from 1 and 6, with the proviso that R$_{18}$, R$_{19}$, R$_{20}$ and R$_{21}$ do not simultaneously represent a hydrogen atom,
r and s, which may be identical or different, are integers ranging from 1 to 6,
q is equal to 0 or to an integer ranging from 1 to 34,
X$^-$ is an anion such as a halide,
A is a divalent radical or preferably is —CH$_2$—CH$_2$—O—CH$_2$—CH$_2$—.

Such compounds are described in particular in EP-A-122,324.

Among these products, mention may be made, for example, of Mirapol® A 15, Mirapol® AD1, Mirapol® AZ1 and Mirapol® 175 marketed by Miranol.

(9) Quaternary polymers of vinylpyrrolidone and of vinylimidazole, such as, for example, the products marketed under the names Luviquat® FC 905, FC 550 and FC 370 by BASF.

(10) Crosslinked methacryloyloxy(C$_1$-C$_4$)alkyltri(C$_1$-C$_4$) alkylammonium salt polymers such as the polymers obtained by homopolymerization of dimethylaminoethyl methacrylate quaternized with methyl chloride, or by copolymerization of acrylamide with dimethylaminoethyl methacrylate quaternized with methyl chloride, the homo- or copolymerization being followed by crosslinking with a compound containing olefinic unsaturation, in particular methylenebisacrylamide. A crosslinked acrylamide/methacryloyloxyethyltrimethylammonium chloride copolymer (20/80 by weight) in the form of a dispersion containing 50% by weight of the said copolymer in mineral oil can be used more particularly. This dispersion is marketed under the name Salcare® SC 92 by Ciba. A crosslinked methacryloyloxyethyltrimethylammonium chloride homopolymer containing about 50% by weight of the homopolymer in mineral oil or in a liquid ester can also be used. These dispersions are marketed under the names Salcare® SC 95 and Salcare® SC 96 by Ciba.

Other cationic polymers that can be used in the context of the invention are cationic proteins or cationic protein hydrolysates, polyalkyleneimines, in particular polyethyleneimines, polymers containing vinylpyridine or vinylpyridinium units, condensates of polyamines and of epichlorohydrin, quaternary polyureylenes and chitin derivatives.

Among all the cationic polymers that may be used in the context of the present invention, it is preferred to use cationic cyclopolymers, in particular the dimethyldiallylammonium chloride homopolymers or copolymers marketed under the names Merquat 100, Merquat 550 and Merquat S by Nalco, and quaternary vinylpyrrolidone and vinylimidazole polymers, and mixtures thereof.

The silicones that may be used in accordance with the invention are in particular polyorganosiloxanes that are insoluble in the composition and that may be in the form of oils, waxes, resins or gums.

The organopolysiloxanes are defined in greater detail in Walter Noll's "Chemistry and Technology of Silicones" (1968) Academic Press. They can be volatile or non-volatile.

When they are volatile, the silicones are more particularly selected from those having a boiling point of from 60° C. and 260° C., and even more particularly from:
(i) cyclic silicones containing from 3 to 7 and preferably 4 to 5 silicon atoms. These are, for example, octamethylcyclotetrasiloxane marketed in particular under the name Volatile Silicone 7207 by Union Carbide or Silbione 70045 V 2 by Rhodia Chimie, decamethylcyclopentasiloxane marketed under the name Volatile Silicone 7158 by Union Carbide, and Silbione 70045 V 5 by Rhodia Chimie, and mixtures thereof.

Mention may also be made of cyclocopolymers of the dimethylsiloxanes/methylalkylsiloxane type, such as Volatile Silicone FZ 3109 marketed by Union Carbide, having the chemical structure:

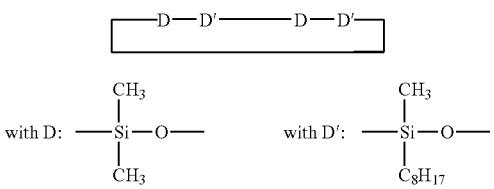

Mention may also be made of mixtures of cyclic silicones with organosilicon compounds, such as the mixture of octamethylcyclotetrasiloxane and tetratrimethylsilylpentaerythritol (50/50) and the mixture of octamethylcyclotetrasiloxane and oxy-1,1'-bis(2,2,2',2',3,3'-hexatrimethylsilyloxy)neopentane;
(ii) linear volatile silicones containing 2 to 9 silicon atoms and having a viscosity of less than or equal to 5×10$^{-6}$ m$^2$/s at 25° C. An example is decamethyltetrasiloxane marketed in particular under the name SH 200 by Toray Silicone. Silicones belonging to this category are also described in the article published in *Cosmetics and Toiletries*, Vol. 91, January 76, pp. 27-32, Todd & Byers "Volatile Silicone Fluids for Cosmetics".

Non-volatile silicones, and more particularly polyalkylsiloxanes, polyarylsiloxanes, polyalkylarylsiloxanes, silicone gums and resins, polyorganosiloxanes modified with organofunctional groups, and mixtures thereof, are preferably used.

These silicones are more particularly selected from polyalkylsiloxanes, among which mention may be made mainly of polydimethylsiloxanes containing trimethylsilyl end groups having a viscosity of from 5×10$^{-6}$ to 2.5 m$^2$/s at 25° C. and preferably 1×10$^{-5}$ to 1 m$^2$/s. The viscosity of the silicones is measured, for example, at 25° C. according to ASTM standard 445 Appendix C.

Among these polyalkylsiloxanes, mention may be made, in a non-limiting manner, of the following commercial products:
the Silbione oils of the 47 and 70 047 series or the Mirasil oils marketed by Rhodia Chimie, such as, for example, the oil 70 047 V 500 000;
the oils of the Mirasil series marketed by Rhodia Chimie;
the oils of the 200 series from the company Dow Corning, such as, more particularly, DC200 with a viscosity of 60,000 cSt;

the Viscasil oils from General Electric and certain oils of the SF series (SF 96, SF 18) from General Electric.

Mention may also be made of polydimethylsiloxanes containing dimethylsilanol end groups (Dimethiconol according to the CTFA name) such as the oils of the 48 series from the company Rhodia Chimie.

In this category of polyalkylsiloxanes, mention may also be made of the products marketed under the names Abil Wax 9800 and 9801 by Goldschmidt, which are poly($C_1$-$C_{20}$) alkylsiloxanes.

The polyalkylarylsiloxanes are selected particularly from linear and/or branched polydimethylmethylphenylsiloxanes and polydimethyldiphenylsiloxanes with a viscosity of from $1 \times 10^{-5}$ to $5 \times 10^{-2}$ m²/s at 25° C.

Among these polyalkylarylsiloxanes, mention may be made, by way of example, of the products marketed under the following names:
the Silbione oils of the 70 641 series from Rhodia Chimie;
the oils of the Rhodorsil 70 633 and 763 series from Rhodia Chimie;
the oil Dow Corning 556 Cosmetic Grade Fluid from Dow Corning;
the silicones of the PK series from Bayer, such as the product PK20;
the silicones of the PN and PH series from Bayer, such as the products PN1000 and PH1000;
certain oils of the SF series from General Electric, such as SF 1023, SF 1154, SF 1250 and SF 1265.

The silicone gums that can be used in accordance with the invention are, in particular, polydiorganosiloxanes with high number-average molecular masses of from 200,000 and 1,000,000, used alone or as a mixture in a solvent. This solvent can be selected from volatile silicones, polydimethylsiloxane (PDMS) oils, polyphenylmethylsiloxane (PPMS) oils, isoparaffins, polyisobutylenes, methylene chloride, pentane, dodecane and tridecane, or mixtures thereof.

Mention may be made more particularly of the following products:
polydimethylsiloxane,
polydimethylsiloxane/methylvinylsiloxane gums,
polydimethylsiloxane/diphenylsiloxane,
polydimethylsiloxane/phenylmethylsiloxane,
polydimethylsiloxane/diphenylsiloxane/methylvinylsiloxane.

Products that can be used more particularly in accordance with the invention are mixtures such as:
mixtures formed from a polydimethylsiloxane hydroxylated at the chain end (referred to as dimethiconol according to the nomenclature in the CTFA dictionary) and from a cyclic polydimethylsiloxane (referred to as cyclomethicone according to the nomenclature in the CTFA dictionary), such as the product Q2 1401 marketed by Dow Corning;
mixtures formed from a polydimethylsiloxane gum with a cyclic silicone, such as the product SF 1214 Silicone Fluid from the company General Electric; this product is an SF 30 gum corresponding to a dimethicone, having a number-average molecular weight of 500,000, dissolved in the oil SF 1202 Silicone Fluid corresponding to decamethylcyclopentasiloxane;
mixtures of two PDMSs with different viscosities, and more particularly of a PDMS gum and a PDMS oil, such as the product SF 1236 from the company General Electric. The product SF 1236 is a mixture of an SE 30 gum defined above, having a viscosity of 20 m²/s, and an SF 96 oil, with a viscosity of $5 \times 10^{-6}$ m²/s. This product preferably contains 15% SE 30 gum and 85% SF 96 oil.

The organopolysiloxane resins that can be used in accordance with the invention are crosslinked siloxane systems containing the following units:

$R_2SiO_{2/2}$, $R_3SiO_{1/2}$, $RSiO_{3/2}$ and $SiO_{4/2}$ in which R is a hydrocarbon-based group containing 1 to 16 carbon atoms or a phenyl group. Among these products, those particularly preferred are the ones in which R is a $C_1$-$C_4$ lower alkyl radical, more particularly methyl, or a phenyl radical.

Among these resins, mention may be made of the product marketed under the name Dow Corning 593 or those marketed under the names Silicone Fluid SS 4230 and SS 4267 by General Electric, which are silicones of dimethyl/trimethyl siloxane structure.

Mention may also be made of the trimethyl siloxysilicate type resins marketed in particular under the names X22-4914, X21-5034 and X21-5037 by Shin-Etsu.

The organomodified silicones that can be used in accordance with the invention are silicones as defined above and comprising in their structure one or more organofunctional groups attached via a hydrocarbon-based radical.

Among the organomodified silicones, mention may be made of polyorganosiloxanes comprising:

polyethyleneoxy and/or polypropyleneoxy groups optionally comprising $C_6$-$C_{24}$ alkyl groups, such as the products known as dimethicone copolyol marketed by Dow Corning under the name DC 1248 or the oils Silwet L 722, L 7500, L 77 and L 711 by Union Carbide, and the ($C_{12}$)alkylmethicone copolyol marketed by Dow Corning under the name Q2 5200;

substituted or unsubstituted amine groups, such as the products marketed under the name GP 4 Silicone Fluid and GP 7100 by Genesee, or the products marketed under the names Q2 8220 and Dow Corning 929 or 939 by Dow Corning. The substituted amine groups are, in particular, $C_1$-$C_4$ aminoalkyl groups;

thiol groups such as the products marketed under the names GP 72 A and GP 71 from Genesee;

alkoxylated groups such as the product marketed under the name Silicone Copolymer F-755 by SWS Silicones and Abil Wax 2428, 2434 and 2440 by Goldschmidt;

hydroxylated groups such as the polyorganosiloxanes containing a hydroxyalkyl function, described in FR-A-85/16334, corresponding to formula (XI):

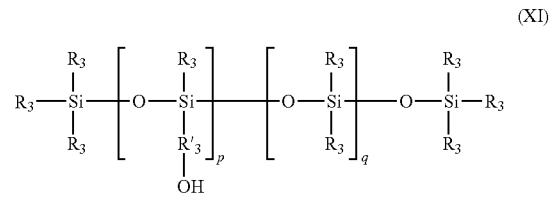

in which the radicals $R_3$, which may be identical or different, are selected from methyl and phenyl radicals; at least 60 mol % of the radicals $R_3$ denoting methyl; the radical $R'_3$ is a $C_2$-$C_{18}$ divalent hydrocarbon-based alkylene chain unit; p is from 1 and 30 inclusive; q is from 1 and 150 inclusive;

acyloxyalkyl groups such as, for example, the polyorganosiloxanes described in U.S. Pat. No. 4,957,732 and corresponding to formula (XII):

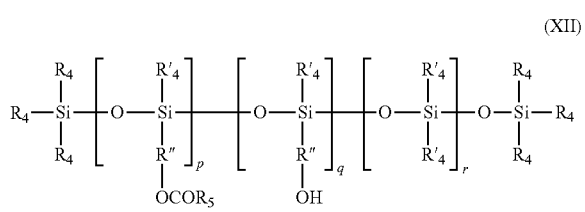
(XII)

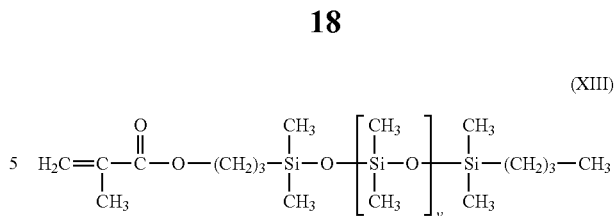
(XIII)

in which:

$R_4$ is a methyl, phenyl, —OCOR$_5$ or hydroxyl group, one of the radicals $R_4$ per silicon atom possibly being OH;

$R'_4$ is methyl or phenyl; at least 60 mol % of all the radicals $R_4$ and $R'_4$ denoting methyl;

$R_5$ is $C_8$-$C_{20}$ alkyl or alkenyl;

R″ is a $C_2$-$C_{18}$ linear or branched divalent hydrocarbon-based alkylene radical;

r is from 1 and 120 inclusive;

p is from 1 and 30;

q is equal to 0 or is less than 0.5 p, p+q being from 1 and 30; the polyorganosiloxanes of formula (XII) may contain groups:

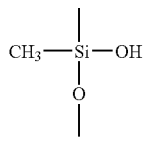

in proportions not exceeding 15% of the sum p+q+r;

anionic groups of carboxylic type, such as, for example, in the products described in EP-186,507 from the company Chisso Corporation, or of alkylcarboxylic type, such as those present in the product X-22-3701E from the company Shin-Etsu; 2-hydroxyalkyl sulfonate; 2-hydroxyalkyl thiosulfate such as the products marketed by Goldschmidt under the names Abil S201 and Abil S255;

hydroxyacylamino groups, such as the polyorganosiloxanes described in EP 342 834. Mention may be made, for example, of the product Q2-8413 from the company Dow Corning.

According to the invention, it is also possible to use silicones comprising a polysiloxane portion and a portion consisting of a non-silicone organic chain, one of the two portions constituting the main chain of the polymer, the other being grafted onto the said main chain. These polymers are described, for example, in EP-A412,704, EP-A412,707, EP-A-640,105, WO 95/00578, EP-A-582,152 and WO 93/23009 and U.S. Pat. Nos. 4,693,935, 4,728,571 and 4,972,037. These polymers are preferably anionic or nonionic.

Such polymers are, for example, copolymers that can be obtained by free-radical polymerization starting with a monomer mixture consisting of:

a) 50 to 90% by weight of tert-butyl acrylate;

b) 0 to 40% by weight of acrylic acid;

c) 5 to 40% by weight of silicone macromer of formula:

with v being a number ranging from 5 to 700; the weight percentages being calculated relative to the total weight of the monomers.

Other examples of grafted silicone polymers are, in particular, polydimethylsiloxanes (PDMS) onto which are grafted, via a connecting chain unit of thiopropylene type, mixed polymer units of poly(meth)acrylic acid type and of polyalkyl (meth)acrylate type and polydimethylsiloxanes (PDMS) onto which are grafted, via a connecting chain unit of thiopropylene type, polymer units of polyisobutyl (meth) acrylate type.

According to the invention, all of the silicones can also be used in the form of emulsions, nanoemulsions or microemulsions.

The polyorganosiloxanes that are particularly preferred in accordance with the invention are:

non-volatile silicones selected from the family of polyalkylsiloxanes containing trimethylsilyl end groups, such as oils having a viscosity of from 0.2 and 2.5 m²/s at 25° C., such as the oils of the DC200 series from Dow Corning, in particular that with a viscosity of 60 000 cSt, of the Silbione 70047 and 47 series and more particularly the oil 70 047 V 500 000, which are marketed by Rhodia Chimie, polyalkylsiloxanes containing dimethylsilanol end groups, such as dimethiconols, or polyalkylarylsiloxanes such as the oil Silbione 70641 V 200 marketed by Rhodia Chimie;

the organopolysiloxane resin marketed under the name Dow Corning 593;

polysiloxanes containing amine groups, such as amodimethicones or trimethylsilylamodimethicones.

The cationic proteins or cationic protein hydrolysates are, in particular, chemically modified polypeptides bearing quaternary ammonium groups at the end of the chain or grafted thereto. Their molecular mass can range, for example, from 1,500 to 10,000 and in particular from 2,000 to 5,000 approximately. Among these compounds, mention may be made in particular of:

collagen hydrolysates bearing triethylammonium groups, such as the products marketed under the name Quat-Pro E by Maybrook and referred to in the CTFA dictionary as "Triethonium Hydrolyzed Collagen Ethosulfate";

collagen hydrolysates bearing trimethylammonium and trimethylstearylammonium chloride groups, marketed under the name Quat-Pro S by Maybrook and referred to in the CTFA dictionary as "Steartrimonium Hydrolyzed Collagen";

animal protein hydrolysates bearing trimethylbenzylammonium groups such as the products marketed under the name Crotein BTA by Croda and referred to in the CTFA dictionary as "Benzyltrimonium hydrolyzed animal protein";

protein hydrolysates bearing, on the polypeptide chain, quaternary ammonium groups containing at least one alkyl radical having from 1 to 18 carbon atoms.

Among these protein hydrolysates, mention may be made, inter alia, of:

Croquat L in which the quaternary ammonium groups contain a $C_{12}$ alkyl group;

Croquat M in which the quaternary ammonium groups contain $C_{10}$-$C_{18}$ alkyl groups;
Croquat S in which the quaternary ammonium groups contain a $C_{18}$ alkyl group;
Crotein Q in which the quaternary ammonium groups contain at least one alkyl group having from 1 to 18 carbon atoms.
These various products are marketed by Croda.

Other quaternized proteins or hydrolysates are, for example, those corresponding to formula (XIV):

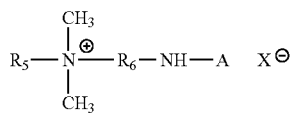

(XIV)

in which $X^-$ is an anion of an organic or mineral acid, A is a protein residue derived from hydrolysates of collagen protein, $R_5$ is a lipophilic group containing up to 30 carbon atoms and $R_6$ is an alkylene group having 1 to 6 carbon atoms. Mention may be made, for example, of the products marketed by Inolex under the name Lexein QX 3000, referred to in the CTFA dictionary as "Cocotrimonium Collagen Hydrolysate".

Mention may also be made of quaternized plant proteins such as wheat, corn or soybean proteins: as quaternized wheat proteins, mention may be made of those marketed by Croda under the names Hydrotriticum WQ or QM, referred to in the CTFA dictionary as "Cocodimonium Hydrolysed Wheat Protein", Hydrotriticum QL, referred to in the CTFA dictionary as "Lauridimonium Hydrolysed Wheat Protein" or Hydrotriticum QS, referred to in the CTFA dictionary as "Steardimonium Hydrolysed Wheat Protein".

According to the present invention, the compounds of ceramide type are in particular natural or synthetic ceramides and/or glycoceramides and/or pseudoceramides and/or neoceramides.

Compounds of ceramide type are described, for example, in DE 4 424 530, DE 4 424 533, DE 4 402 929, DE 4 420 736, WO 95/23807, WO 94/07844, EP-A-0 646 572, WO 95/16665, FR-2 673 179, EP-A-0 227 994, WO 94/07844, WO 94/24097 and WO 94/10131, the teachings of which are included herein by way of reference.

Compounds of ceramide type that are particularly preferred according to the invention are, for example:
2-N-linoleoylaminooctadecane-1,3-diol,
2-N-oleoylaminooctadecane-1,3-diol,
2-N-palmitoylaminooctadecane-1,3-diol,
2-N-stearoylaminooctadecane-1,3-diol,
2-N-behenoylaminooctadecane-1,3-diol,
2-N-[2-hydroxypalmitoyl]aminooctadecane-1,3-diol,
2-N-stearoylaminooctadecane-1,3,4-triol and in particular N-stearoylphytosphingosine,
2-N-palmitoylaminohexadecane-1,3-diol,
bis(N-hydroxyethyl-N-cetyl)malonamide,
N-(2-hydroxyethyl)-N-(3-cetyloxy-2-hydroxypropyl)cetylamide,
N-docosanoyl-N-methyl-D-glucamine,
or mixtures of these compounds.

It is also possible to use cationic surfactants, among which mention may be made in particular of: optionally polyoxyalkylenated primary, secondary or tertiary fatty amine salts; quaternary ammonium salts; imidazoline derivatives; or amine oxides of cationic nature.

Examples of quaternary ammonium salts include:
those of general formula (XV) below:

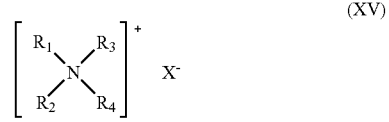

(XV)

in which the radicals $R_1$ to $R_4$, which may be identical or different, represent a linear or branched aliphatic radical containing from 1 to 30 carbon atoms, or an aromatic radical such as aryl or alkylaryl. The aliphatic radicals can comprise heteroatoms such as, in particular, oxygen, nitrogen, sulfur or halogens. The aliphatic radicals are selected, for example, from alkyl, alkoxy, polyoxy($C_2$-$C_6$)alkylene, alkylamide, ($C_{12}$-$C_{22}$)alkylamido($C_2$-$C_6$)alkyl, ($C_{12}$-$C_{22}$)alkylacetate and hydroxyalkyl radicals, comprising from about 1 to 30 carbon atoms; $X^-$ is an anion selected from the group of halides, phosphates, acetates, lactates, ($C_2$-$C_6$)alkyl sulfates and alkyl or alkylaryl sulfonates;
quaternary ammonium salts of imidazolinium, such as, for example, the salt of formula (XVI) below:

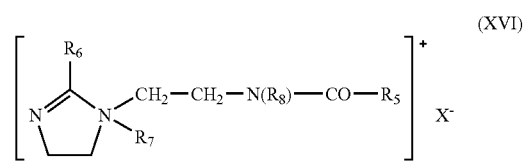

(XVI)

in which $R_5$ is an alkenyl or alkyl radical containing from 8 to 30 carbon atoms, for example tallow fatty acid derivatives, $R_6$ is a hydrogen atom, a $C_1$-$C_4$ alkyl radical or an alkenyl or alkyl radical containing from 8 to 30 carbon atoms, $R_7$ is a $C_1$-$C_4$ alkyl radical, $R_8$ is a hydrogen atom or a $C_1$-$C_4$ alkyl radical, $X^-$ is an anion selected from the group of halides, phosphates, acetates, lactates, alkyl sulfates and alkyl or alkylaryl sulfonates. $R_5$ and $R_6$ preferably is a mixture of alkenyl or alkyl radicals containing from 12 to 21 carbon atoms, for example tallow fatty acid derivatives, $R_7$ is a methyl radical and $R_8$ is a hydrogen atom. Such a product is marketed, for example, under the name "Rewoquat W 75" by Degussa;
diquaternary ammonium salts of formula (XVII):

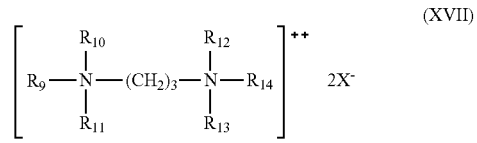

(XVII)

in which $R_9$ is an aliphatic radical containing from about 16 to 30 carbon atoms, $R_{10}$, $R_{11}$, $R_{12}$, $R_{13}$ and $R_{14}$, which may be identical or different, are selected from hydrogen or an alkyl radical containing from 1 to 4 carbon atoms, and $X^-$ is an anion selected from the group of halides, acetates, phosphates, nitrates and methyl sulfates. Such diquaternary ammonium salts in particular comprise propane tallow diammonium dichloride;
quaternary ammonium salts containing at least one ester function.

The quaternary ammonium salts containing at least one ester function that may be used according to the invention are, for example, those of formula (XVIII) below:

$$R_{17}\overset{O}{\underset{\|}{C}}-(OC_nH_{2n})_y-\underset{\underset{R_{15}}{|}}{\overset{(C_rH_{2r}O)_z-R_{18}}{\overset{|}{N^+}}}-(C_pH_{2p}O)_x R_{16}, \quad X^- \qquad (XVIII)$$

in which:

$R_{15}$ is selected from $C_1$-$C_6$ alkyl radicals and $C_1$-$C_6$ hydroxyalkyl or dihydroxyalkyl radicals;

$R_{16}$ is selected from:
 a radical $$R_{19}\overset{O}{\underset{\|}{-C-}}$$

linear or branched, saturated or unsaturated $C_1$-$C_{22}$ hydrocarbon-based radicals $R_{20}$,
a hydrogen atom, $R_{18}$ is selected from:
 a radical $$R_{21}\overset{O}{\underset{\|}{-C-}}$$

linear or branched, saturated or unsaturated $C_1$-$C_6$ hydrocarbon-based radicals $R_{22}$,
a hydrogen atom, $R_{17}$, $R_{19}$ and $R_{21}$, which may be identical or different, are selected from linear or branched, saturated or unsaturated $C_7$-$C_{21}$ hydrocarbon-based radicals;

n, p and r, which may be identical or different, are integers ranging from 2 to 6;

y is an integer ranging from 1 to 10;

x and z, which may be identical or different, are integers ranging from 0 to 10;

$X^-$ is a simple or complex, organic or inorganic anion;

with the proviso that the sum x+y+z is from 1 to 15, that when x is 0, then $R_{16}$ is $R_{20}$ and that when z is 0, then $R_{18}$ is $R_{22}$.

The $R_{15}$ alkyl radicals may be linear or branched and more particularly linear.

$R_{15}$ preferably is a methyl, ethyl, hydroxyethyl or dihydroxypropyl radical and more particularly a methyl or ethyl radical.

The sum x+y+z is advantageously from 1 to 10.

When $R_{16}$ is a hydrocarbon-based radical $R_{20}$, it may be long and contain from 12 to 22 carbon atoms, or short and contain from 1 to 3 carbon atoms.

When $R_{18}$ is a hydrocarbon-based radical $R_{22}$, it preferably contains 1 to 3 carbon atoms.

$R_{17}$, $R_{19}$ and $R_{21}$, which may be identical or different, are advantageously selected from linear or branched, saturated or unsaturated $C_{11}$-$C_{21}$ hydrocarbon-based radicals, and more particularly from linear or branched, saturated or unsaturated, $C_{11}$-$C_{21}$ alkyl and alkenyl radicals.

x and z, which may be identical or different, are preferably 0 or 1.

y is advantageously equal to 1.

n, p and r, which may be identical or different, are preferably 2 or 3 and even more particularly are equal to 2.

The anion is preferably a halide (chloride, bromide or iodide) or an alkyl sulfate, more particularly methyl sulfate. However, methanesulfonate, phosphate, nitrate, tosylate, an anion derived from an organic acid, such as acetate or lactate, or any other anion that is compatible with the ammonium containing an ester function, may be used.

The anion $X^-$ is even more particularly chloride or methyl sulfate.

The ammonium salts more particularly used are those of formula (XVIII) in which:

$R_{15}$ is a methyl or ethyl radical, x and y are equal to 1;

z is equal to 0 or 1;

n, p and r are equal to 2;

$R_{16}$ is selected from:
 a radical $$R_{19}\overset{O}{\underset{\|}{-C-}}$$

methyl, ethyl or $C_{14}$-$C_{22}$ hydrocarbon-based radicals;
a hydrogen atom;

$R_{18}$ is selected from:

$$R_{21}\overset{O}{\underset{\|}{-C-}}$$

a radical
a hydrogen atom;

$R_{17}$, $R_{19}$ and $R_{21}$, which may be identical or different, are selected from linear or branched, saturated or unsaturated $C_{13}$-$C_{17}$ hydrocarbon-based radicals and preferably from linear or branched, saturated or unsaturated $C_{13}$-$C_{17}$ alkyl and alkenyl radicals.

The hydrocarbon-based radicals are advantageously linear.

Examples that may be mentioned include the compounds of formula (XVI) such as the diacyloxyethyldimethylammonium, diacyloxyethylhydroxyethylmethylammonium, monoacyloxyethyldihydroxyethylmethylammonium, triacyloxyethylmethylammonium and monoacyloxyethylhydroxyethyldimethylammonium salts (chloride or methyl sulfate in particular), and mixtures thereof. The acyl radicals preferably contain 14 to 18 carbon atoms and are obtained more particularly from a plant oil such as palm oil or sunflower oil. When the compound contains several acyl radicals, these radicals may be identical or different.

These products are obtained, for example, by direct esterification of triethanolamine, triisopropanolamine, an alkyldiethanolamine or an alkyldiisopropanolamine, which are optionally oxyalkylenated, with fatty acids or with fatty acid mixtures of plant or animal origin, or by transesterification of the methyl esters thereof. This esterification is followed by a quaternization using an alkylating agent such as an alkyl halide (preferably a methyl or ethyl halide), a dialkyl sulfate (preferably dimethyl or diethyl sulfate), methyl methanesulfonate, methyl para-toluenesulfonate, glycol chlorohydrin or glycerol chlorohydrin.

Such compounds are marketed, for example, under the names Dehyquart by Cognis, Stepanquat by Stepan, Noxamium by CECA or Rewoquat WE 18 by Degussa.

It is also possible to use the ammonium salts containing at least one ester function that are described in U.S. Pat. Nos. 4,874,554 and 4,137,180.

Among the quaternary ammonium salts of formula (XV), the ones that are preferred are, on the one hand, tetraalkylammonium chlorides such as, for example, dialkyldimethylammonium chlorides or alkyltrimethylammonium chlorides, in which the alkyl radical contains from about 12 to 22 carbon atoms, in particular behenyltrimethylammonium chloride, distearyldimethylammonium chloride, cetyltrimethylammonium chloride, or benzyldimethylstearylammonium chloride, or, on the other hand, stearamidopropyidimethyl(myristyl acetate)ammonium chloride marketed under the name Ceraphyl 70 by Van Dyk.

The fatty acids are selected more particularly from myristic acid, palmitic acid, stearic acid, behenic acid, oleic acid, linoleic acid, linolenic acid and isostearic acid.

The fatty acid derivatives are especially carboxylic acid esters, in particular mono-, di-, tri- or tetracarboxylic esters.

The monocarboxylic acid esters are, in particular, linear or branched, saturated or unsaturated $C_1$-$C_{26}$ aliphatic acid monoesters of linear or branched, saturated or unsaturated, $C_1$-$C_{26}$ aliphatic alcohols, the total carbon number of these esters being greater than or equal to 10.

Among the monoesters, mention may be made of dihydroabietyl behenate; octyldodecyl behenate; isocetyl behenate; cetyl lactate; $C_{12}$-$C_{15}$ alkyl lactate; isostearyl lactate; lauryl lactate; linoleyl lactate; oleyl lactate; (iso)stearyl octanoate; isocetyl octanoate; octyl octanoate; cetyl octanoate; decyl oleate; isocetyl isostearate; isocetyl laurate; isocetyl stearate; isodecyl octanoate; isodecyl oleate; isononyl isononanoate; isostearyl palmitate; methylacetyl ricinoleate; myristyl stearate; octyl isononanoate; 2-ethylhexyl isononate; octyl palmitate; octyl pelargonate; octyl stearate; octyldodecyl erucate; oleyl erucate; ethyl and isopropyl palmitates, 2-ethylhexyl palmitate, 2-octyldecyl palmitate, alkyl myristates such as isopropyl, butyl, cetyl or 2-octyldodecyl myristate, hexyl stearate, butyl stearate, isobutyl stearate; dioctyl malate, hexyl laurate, 2-hexyldecyl laurate, isostearyl neopentanoate, isodecyl neopentanoate.

$C_4$-$C_{22}$ di- or tricarboxylic acid esters of $C_1$-$C_{22}$ alcohols and mono-, di- or tricarboxylic acid esters of $C_2$-$C_{26}$ di-, tri-, tetra- or pentahydroxy alcohols can also be used.

Mention may be made in particular of: diethyl sebacate; diisopropyl sebacate; diisopropyl adipate; di-n-propyl adipate; dioctyl adipate; diisostearyl adipate; dioctyl maleate; glyceryl undecylenate; octyidodecylstearoyl stearate; pentaerythrityl monoricinoleate; pentaerythrityl tetraisononanoate; pentaerythrityl tetrapelargonate; pentaerythrityl tetraisostearate; pentaerythrityl tetraoctanoate; propylene glycol dicaprylate dicaprate; tridecyl erucate; triisopropyl citrate; triisostearyl citrate; glyceryl trilactate; glyceryl trioctanoate; trioctyldodecyl citrate; trioleyl citrate.

Among the esters mentioned above, it is preferred to use ethyl and isopropyl palmitates, 2-ethylhexyl palmitate, 2-octyidecyl palmitate, alkyl myristates such as isopropyl, butyl, cetyl or 2-octyidodecyl myristate, hexyl stearate, butyl stearate, isobutyl stearate; dioctyl malate, hexyl laurate, 2-hexyldecyl laurate, isononyl isononanoate, cetyl octanoate, isostearyl neopentanoate, isodecyl neopentanoate.

The fluoro oils are, for example, the perfluoropolyethers described in particular in EP-A-486,135 and the fluorohydrocarbon compounds described in particular in WO 93/11103. The teaching of these two patent applications is included in its entirety in the present application by way of reference.

The term "fluorohydrocarbon compounds" is compounds whose chemical structure contains a carbon skeleton in which certain hydrogen atoms have been replaced with fluorine atoms.

The fluoro oils can also be fluorocarbons such as fluoroamines, for example perfluorotributylamine, fluorohydrocarbons, for example perfluorodecahydronaphthalene, fluoro esters and fluoro ethers.

The perfluoropolyethers are marketed, for example, under the trademarks Fomblin by Montefluos and Krytox by Du Pont.

Among the fluorohydrocarbon compounds, mention may also be made of fluorine-containing fatty acid esters such as the product marketed under the name Nofable FO by Nippon Oil.

Needless to say, it is possible to use mixtures of conditioning agents.

According to the invention, the conditioning agent(s) may represent from 0.001% to 20% by weight, preferably from 0.01% to 10% by weight and more particularly from 0.1% to 3% by weight, relative to the total weight of the final composition.

The compositions according to the invention may be in the form of aqueous or aqueous-alcoholic haircare lotions. The cosmetic compositions according to the invention may also be in the form of a gel, a milk, a cream, an emulsion or a mousse, and may be used on the hair.

The compositions may be packaged in various forms and especially in vaporizers, pump-dispenser bottles or in aerosol containers in order to apply the composition in vaporized form or in the form of a mousse. Such packaging forms are indicated, for example, when it is desired to obtain a spray, a lacquer or a mousse for treating the hair.

The pH of the composition applied to the keratin fibers generally ranges from 1 to 11. It is preferably from 2 to 6, and may be adjusted to the desired value by means of acidifying or basifying agents that are well known in the prior art for compositions applied to keratin fibers.

Among the basifying agents that may be mentioned, for example, are aqueous ammonia, alkali metal carbonates, alkanolamines such as monoethanolamine, diethanolamine and triethanolamine and also derivatives thereof, oxyethylenated and/or oxypropylenated hydroxyalkylamines and ethylenediamines, sodium hydroxide, potassium hydroxide and the compounds having the following formula:

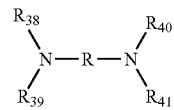

in which R is a propylene residue optionally substituted with a hydroxyl group or a $C_1$-$C_4$ alkyl radical; $R_{38}$, $R_{39}$, $R_{40}$ and $R_{41}$, which may be identical or different, represent a hydrogen atom, a $C_1$-$C_4$ alkyl radical or a $C_1$-$C_4$ hydroxyalkyl radical.

The acidifying agents are conventionally, for example, mineral or organic acids, for instance hydrochloric acid, orthophosphoric acid, carboxylic acids, for instance tartaric acid, citric acid or lactic acid, or sulfonic acids.

According to one particular embodiment, the treatment process is applied to keratin fibers, in particular hair dyed by direct dyeing or oxidation dyeing.

Another aspect of the invention entails the use of the said process for protecting keratin fibers against the action of atmospheric agents and especially against the action of light.

This invention features the use of the said process as a post-treatment to oxidation dyeing or direct dyeing of keratin fibers and more particularly of the hair.

The present invention also features a process for dyeing keratin fibers, in particular human hair, comprising at least steps a), b) and c) below:
a) direct dyeing or oxidation dyeing of the said fibers is performed,
b) a composition comprising, in a physiologically acceptable and in particular a cosmetically acceptable medium, at least one protective agent with a log P of less than or equal to 6 is applied to the said fibers,
c) a heating iron at a temperature of greater than or equal to 60° C. is applied to the said fibers; the order of steps a) and b) being irrelevant and step c) being performed after step a) or step b) on condition that step b) has already been performed.

One particular process mode for dyeing fibers comprises the following steps:
1) a direct or oxidation dye composition (A) is applied to the said fibers a) for a time that is sufficient to develop the color,
2) optionally, the said fibers are then rinsed and/or washed with shampoo and/or partially or totally dried,
3) a composition (B) comprising a protective agent as defined above is applied,
4) optionally, the said fibers are then rinsed and/or washed with shampoo and/or partially or totally dried,
5) a heating iron at a temperature of greater than or equal to 60° C. is applied to the fibers,
6) optionally, the said fibers are then rinsed and/or washed with shampoo and/or partially or totally dried.

A second particular process mode for dyeing fibers comprises the following steps:
1) a composition (B) comprising a protective agent as defined above is applied,
2) the said fibers are optionally rinsed and/or washed with shampoo and/or partially or totally dried,
3) a heating iron at a temperature of greater than or equal to 60° C. is applied to the fibers,
4) a direct or oxidation dye composition (A) is applied to the said fibers a) for a time that is sufficient to develop the color,
5) the said fibers are optionally rinsed and/or washed with shampoo and/or partially or totally dried,
6) optionally, the said fibers are then rinsed and/or washed with shampoo and/or partially or totally dried.

A third particular process mode for dyeing fibers comprises the following steps:
1) a composition (B) comprising a protective agent as defined above is applied,
2) the said fibers are optionally rinsed and/or washed with shampoo and/or partially or totally dried,
3) a direct or oxidation dye composition (A) is applied to the said fibers a) for a time that is sufficient to develop the color,
4) the said fibers are optionally rinsed and/or washed with shampoo and/or partially or totally dried,
5) a heating iron at a temperature of greater than or equal to 60° C. is applied to the fibers,
6) optionally, the said fibers are then rinsed and/or washed with shampoo and/or partially or totally dried.

In the various dyeing process modes, the composition (B) comprising the protective agent(s) may be applied immediately after dyeing, or after a delay. The term "after a delay" refers to an application made a few hours, one day or several days (from 1 to 60 days) after the dyeing operation. Composition (B) will preferably be applied immediately after dyeing the keratin fibers.

The nature and concentration of the dyes present in the dye composition (A) is not critical.

In the case of lightening direct dyeing operations, the dye compositions (A) result from the mixing, at the time of use, of a dye composition (A1) containing at least one direct dye and a composition (A2) containing an oxidizing agent.

In the case of oxidation dyeing, the dye compositions (A) result from the mixing, at the time of use, of a dye composition (A1) containing at least one oxidation base and optionally at least one coupler and/or a direct dye and of a composition (A2) containing an antioxidant.

The direct dyes are more particularly compounds that absorb light radiation in the visible range (400-750 nm). They may be of nonionic, anionic or cationic nature.

Generally, the direct dyes are selected from nitrobenzene dyes and azo, anthraquinone, naphthoquinone, benzoquinone, phenothiazine, indigoid, xanthene, phenanthridine, phthalocyanin and triarylmethane-based dyes, alone or as mixtures.

Among the nitrobenzene dyes that may be mentioned are the following red or orange compounds: 1-hydroxy-3-nitro-4-N-(γ-hydroxypropyl)aminobenzene, N-(β-hydroxyethyl)amino-3-nitro-4-aminobenzene, 1-amino-3-methyl-4-N-(β-hydroxyethyl)amino-6-nitrobenzene, 1-hydroxy-3-nitro-4-N-(β-hydroxyethyl)aminobenzene, 1,4-diamino-2-nitrobenzene, 1-amino-2-nitro-4-methylaminobenzene, N-(β-hydroxyethyl)-2-nitro-para-phenylenediamine, 1-amino-2-nitro-4-(β-hydroxyethyl)amino-5-chlorobenzene, 2-nitro-4-aminodiphenylamine, 1-amino-3-nitro-6-hydroxybenzene, 1-(β-aminoethyl)amino-2-nitro-4-(β-hydroxyethyloxy)benzene, 1-(β,γ-dihydroxypropyl)oxy-3-nitro-4-(β-hydroxyethyl)aminobenzene, 1-hydroxy-3-nitro-4-aminobenzene, 1-hydroxy-2-amino-4,6-dinitrobenzene, 1-methoxy-3-nitro-4-(β-hydroxyethyl)aminobenzene, 2-nitro-4'-hydroxydiphenylamine, 1-amino-2-nitro-4-hydroxy-5-methylbenzene, alone or as mixtures.

As regards the nitrobenzene direct dyes, use may be made of dyes of yellow and green-yellow type, for instance 1-β-hydroxyethyloxy-3-methylamino-4-nitrobenzene, 1-methylamino-2-nitro-5-(β,γ-dihydroxypropyl)oxybenzene, 1-(β-hydroxyethyl)amino-2-methoxy-4-nitrobenzene, 1-(β-aminoethyl)amino-2-nitro-5-methoxybenzene, 1,3-bis(β-hydroxyethyl)amino-4-nitro-6-chlorobenzene, 1-amino-2-nitro-6-methylbenzene, 1-(β-hydroxyethyl)amino-2-hydroxy-4-nitrobenzene, N-(β-hydroxyethyl)-2-nitro-4-trifluoromethylaniline, 4-(β-hydroxyethyl)amino-3-nitrobenzenesulfonic acid, 4-ethylamino-3-nitrobenzoic acid, 4-β-hydroxyethyl)amino-3-nitrochlorobenzene, 4-(β-hydroxyethyl)amino-3-nitromethylbenzene, 4-(β,γ-dihydroxypropyl)amino-3-nitrotrifluoromethylbenzene, 1-(β-ureidoethyl)amino-4-nitrobenzene, 1,3-diamino-4-nitrobenzene, 1-hydroxy-2-amino-5-nitrobenzene, 1-amino-2-[tris(hydroxymethyl)methyl]amino-5-nitrobenzene, 1-(β-hydroxyethyl)amino-2-nitrobenzene and 4-(β-hydroxyethyl)amino-3-nitrobenzamide.

Blue or violet nitrobenzene dyes may also be used, for instance, inter alia, 1-(β-hydroxyethyl)amino-4-N,N-bis(β-hydroxyethyl)amino-2-nitrobenzene, 1-(γ-hydroxypropyl)amino-4-N,N-bis(β-hydroxyethyl)amino-2-nitrobenzene, 1-(β-hydroxyethyl)amino-4-(N-methyl, N-β-hydroxyethyl)amino-2-nitrobenzene, 1-(β-hydroxyethyl)amino-4-(N-ethyl, N-β-hydroxyethyl)amino-2-nitrobenzene, 1-(β,γ-dihydroxypropyl)amino-4-(N-ethyl, N-β-hydroxyethyl)amino-2-nitrobenzene, the 2-nitro-para-phenylenediamines of the following formula:

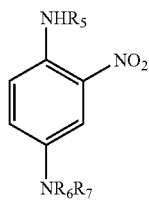

in which:

R$_6$ is a C$_1$-C$_4$ alkyl radical or a β-hydroxyethyl, β-hydroxypropyl or γ-hydroxypropyl radical;

R$_5$ and R$_7$, which may be identical or different, represent a β-hydroxyethyl, β-hydroxypropyl, γ-hydroxypropyl or β,γ-dihydroxypropyl radical, at least one of the radicals R$_6$, R$_7$ or R$_5$ representing a γ-hydroxypropyl radical and R$_6$ and R$_7$ not being able simultaneously to is a β-hydroxyethyl radical when R$_6$ is a γ-hydroxypropyl radical, such as those described in FR-2-692,572.

It is recalled that azo dyes are compounds comprising in their structure at least one —N=N— sequence not included in a ring; methine dyes are compounds comprising in their structure at least one —C=C— sequence not included in a ring; azomethine dyes are compounds comprising in their structure at least one —C=N— sequence not included in a ring.

The triarylmethane-based dyes comprise in their structure at least one sequence below:

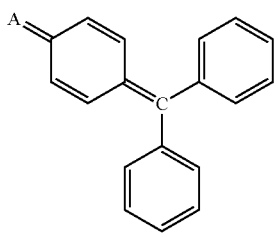

A denoting an oxygen or nitrogen atom.

The xanthene dyes comprise in their structure at least one sequence of formula:

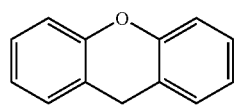 [SMILES: c1ccc2c(c1)Cc1ccccc1O2]

The phenanthridine dyes comprise in their structure at least one sequence of formula:

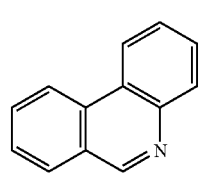 [SMILES: c1ccc2c(c1)cnc1ccccc12]

The phthalocyanin dyes comprise in their structure at least one sequence of formula:

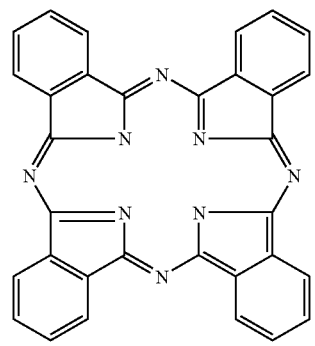 [SMILES: c1ccc2c(c1)-c1nc-2nc2[nH]c(nc3nc(nc4[nH]c(n1)c1ccccc41)-c1ccccc1-3)c1ccccc21]

The phenothiazine dyes comprise in their structure at least one sequence below:

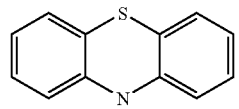 [SMILES: c1ccc2c(c1)Nc1ccccc1S2]

The direct dyes may moreover be selected from basic dyes like those listed in the Color Index, 3rd edition, especially under the names "Basic Brown 16", "Basic Brown 17", "Basic Yellow 57", "Basic Red 76", "Basic Violet 100", "Basic Blue 26" and "Basic Blue 99"; or from the acidic direct dyes listed in the Color Index, 3rd edition, under the names "Acid Orange 7", "Acid Orange 24", "Acid Yellow 36", "Acid Red 33", "Acid Red 184", "Acid Black 2", "Acid Violet 43", and "Acid Blue 62", or cationic direct dyes such as those described in WO 95/01772, WO 95/15144 and EP-714,954, and in particular "Basic Red 51", "Basic Orange 31" and "Basic Yellow 87", the content of which forms an integral part of the present invention.

When they are present, the direct dye(s) preferably represent(s) from 0.0005% to 12% by weight approximately relative to the total weight of the dye composition and even more preferably from 0.005% to 6% by weight approximately relative to this weight.

The oxidation bases may be selected from the oxidation bases conventionally used in oxidation dyeing and among which mention may be made especially of para-phenylenediamines, bis(phenyl)alkylenediamines, para-aminophenols, ortho-aminophenols and heterocyclic bases.

Among the para-phenylenediamines that may more particularly be mentioned, are para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, N,N-diethyl-4-amino-3-methylaniline, N,N-bis(β-hydroxyethyl)-para-phenylenediamine, 4N,N-bis(β-hydroxyethyl)amino-2-methylaniline, 4N,N-bis(β-hydroxyethyl)amino-2-chloroparaaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-paraphenylenediamine, 2-β-hydroxyethyloxy-para-phenylenediamine, 2-β-acetylaminoethyloxy-para-phenylenediamine and N-(β-methoxyethyl)-para-phenylenediamine, and the addition salts thereof with an acid.

Among the para-phenylenediamines mentioned above, para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the addition salts thereof with an acid, are very particularly preferred.

Among the bis(phenyl)alkylenediamines that may more particularly be mentioned, for example, are N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4'-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,5-dioxaoctane, and the addition salts thereof with an acid.

Among the para-aminophenols that may more particularly be mentioned, for example, are para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the addition salts thereof with an acid.

Among the ortho-aminophenols that may more particularly be mentioned, for example, are 2-aminophenol, 2-amino-5-methylphenol, 2-amino-6-methylphenol and 5-acetamido-2-aminophenol, and the addition salts thereof with an acid.

Among the heterocyclic bases that may more particularly be mentioned, for example, are pyridine derivatives, pyrimidine derivatives and pyrazole derivatives.

Among the pyridine derivatives that may more particularly be mentioned are the compounds described, for example, in GB-1-026,978 and GB-1-153,196, such as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine and 3,4-diaminopyridine, and the addition salts thereof with an acid.

Among the pyrimidine derivatives that may more particularly be mentioned are the compounds described, for example, in DE-2-359,399; JP 88-169571; JP 05-163124; EP-0-770,375 or WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, and pyrazolopyrimidine derivatives such as those mentioned in FR-A-2 750 048 and among which mention may be made of pyrazolo[1,5-a]pyrimidine-3,7-diamine; 2,5-dimethylpyrazolo[1,5-a]pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]pyrimidin-7-ol; 3-aminopyrazolo[1,5-a]pyrimidin-5-ol; 2-(3-aminopyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)(2-hydroxyethyl)amino]ethanol, 2-[(7-aminopyrazolo[1,5-a]pyrimidin-3-yl)(2-hydroxyethyl)amino]ethanol, 5,6-dimethylpyrazolo[1,5-a]pyrimidine-3,7-diamine, 2,6-dimethylpyrazolo[1,5-a]pyrimidine-3,7-diamine, 2,5,N7,N7-tetramethylpyrazolo[1,5-a]pyrimidine-3,7-diamine and 3-amino-5-methyl-7-imidazolylpropylaminopyrazolo[1,5-a]pyrimidine, and the addition salts thereof with an acid and the tautomeric forms thereof, when a tautomeric equilibrium exists.

Among the pyrazole derivatives that may more particularly be mentioned are the compounds described in DE-3-843,892 and DE4-133,957 and WO 94/08969, WO 94/08970, FR-A-2,733,749 and DE-195,43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl)amino-1-methylpyrazole, and the addition salts thereof with an acid.

When they are used, these oxidation bases preferably represent from 0.0005% to 12% by weight approximately relative to the total weight of the dye composition, and even more preferably from 0.005% to 6% by weight approximately relative to this weight.

The oxidation dye compositions in accordance with the invention may also contain at least one coupler and/or at least one-direct dye, especially to modify the shades or to enrich them with tints.

The couplers that may be used in the oxidation dye compositions in accordance with the invention may be selected from the couplers conventionally used in oxidation dyeing, and among which mention may be made especially of meta-phenylenediamines, meta-aminophenols, meta-diphenols, naphthols and heterocyclic couplers, for instance indole derivatives, indoline derivatives, pyridine derivatives, indazole derivatives, pyrazolo[1,5-b]-1,2,4-triazole derivatives, pyrazolo[3,2-c]-1,2,4-triazole derivatives, benzimidazole derivatives, benzothiazole derivatives, benzoxazole derivatives, 1,3-benzodioxole derivatives and pyrazolones, and the addition salts thereof with an acid.

These couplers are more particularly selected from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, sesamol, α-naphthol, 2-methyl-1-naphthol, 6-hydroxyindole, 4-hydroxyindole, 4-hydroxy-N-methylindole, 6-hydroxyindoline, 6-hydroxybenzomorpholine, 3,5-diamino-2,6-dimethoxypyridine, 1-N(β-hydroxyethyl)amino-3,4-methylenedioxy-benzene, 2,6-bis(β-hydroxyethyleneamino)toluene, 2,6-dihydroxy-4-methylpyridine, 1H-3-methylpyrazol-5-one, 1-phenyl-3-methylpyrazol-5-one, and the addition salts thereof with an acid.

When they are present, the coupler(s) preferably represent(s) from 0.0001% to 10% by weight approximately relative to the total weight of the dye composition, and even more preferably from 0.005% to 5% by weight approximately relative to this weight.

The dye compositions in accordance with the invention may also contain various adjuvants conventionally used in hair dye compositions, such as anionic, cationic, nonionic, amphoteric or zwitterionic surfactants or mixtures thereof, anionic, cationic, nonionic, amphoteric or zwitterionic polymers or mixtures thereof, mineral or organic thickeners, antioxidants, penetrants, sequestrants, fragrances, buffers, dispersants, conditioning agents, for instance silicones, film-forming agents, preservatives and opacifiers.

Needless to say, one skilled in this art will take care to select this or these optional additional compound(s) such that the advantageous properties intrinsically associated with the oxidation dye composition in accordance with the invention are not, or are not substantially, adversely affected by the envisaged addition(s).

The dye compositions according to the invention may be in various forms, such as in the form of liquids, creams or gels, or in any other form that is suitable for dyeing keratin fibers, and especially human hair.

The nature of the oxidizing agent used in the lightening direct dyeing operation (direct dyeing with an oxidizing agent) or in the oxidation dyeing operation is not critical.

The oxidizing agent is preferably selected from the group formed by hydrogen peroxide, urea peroxide, alkali metal bromates or ferricyanides, and persalts such as perborates and persulfates. One or more redox enzymes such as laccases, peroxidases and two-electron oxidoreductases (such as uricase) may also be used, where appropriate in the presence of the respective donor or cofactor thereof.

According to one particular mode of the invention, the process of the invention may be used on hair that has been sensitized by hair treatments other than those of the invention that are mentioned above.

In order to further illustrate the present invention and the advantages thereof, the following specific examples are given, it being understood that same are intended only as illustrative and in nowise limitative. In said examples to follow, all parts and percentages are given by weight, unless otherwise indicated. In the examples, AM means active material.

EXAMPLES

Example 1

Dyeing Step:

At the time of use, the composition of Table 1 below is mixed weight-for-weight with aqueous hydrogen peroxide solution (L'Oréal professional 20-volumes aqueous hydrogen peroxide solution, at 6%).

The mixture is then applied to locks of permanent-waved hair containing 90% white hairs. The leave-on time is 15 minutes on each side of the lock. The dyeing is then stopped by rinsing with water.

TABLE 1

| (1) Dye composition 1 | ii. Amounts in grams |
|---|---|
| Oleyl alcohol polyglycerolated with 2 mol of glycerol | 4 |
| Oleyl alcohol polyglycerolated with 4 mol of glycerol (78% AM) | 5.69 |
| Oleic acid | 3 |

TABLE 1-continued

| (1) Dye composition 1 | ii. Amounts in grams |
|---|---|
| Oleylamine 2 EO marketed under the name Ethomeen O12 by Akzo 7 g | 7 |
| Dimethaminopropyl laurylaminosuccinamate, sodium salt, at 55% AM | 3 |
| Oleyl alcohol | 5 |
| Oleic acid diethanolamide | 12 |
| Propylene glycol | 3.5 |
| Ethyl alcohol | 7 |
| Dipropylene glycol | 0.5 |
| Propylene glycol monomethyl ether | 9 |
| Sodium metabisulfite as an aqueous solution containing 35% AM | 0.455 |
| Ammonium acetate | 0.8 |
| Antioxidant, sequestrant | qs |
| Fragrance, preservative | qs |
| Aqueous ammonia containing 20% $NH_3$ | 10 |
| Demineralized water | qs 100 |

2. Protective Treatment Steps:

A protective treatment is performed on the dyed locks by applying composition 2 indicated in the table below, at a rate of 2 g/g of hair. The composition is left on for 10 minutes, and a heating smoothing iron at a temperature of 100° C. is then applied by sliding along the fibers.

TABLE 2

| iii. Composition 2 | Amounts in grams |
|---|---|
| Benzyl alcohol | 4.0 g |
| Benzoic acid | 0.2 g |
| Benzophenone-4 | 5.0 g |
| Citric acid/trisodium citrate/triethanolamine buffer | qs pH = 4 |
| Hydroxyethylcellulose | 1.2 g |
| Xanthan gum | 0.4 g |
| Preservatives | qs |
| Water | qs 100 g |

The locks are then washed with DOP camomile shampoo and dried.

UV/visible Light Exposure Steps:

The dyed and treated locks are then exposed to UV/visible light in the visible range over half their length, for a period of 18 h, with a solar simulator Xenon lamp that reproduces a reproducible light spectrum similar to that of sunlight (Suntest XLS marketed by Atlas). The other half of the lock is masked with card.

Evaluation of the Photoprotection:

The degradation of the color after exposure to UV/visible light is evaluated visually from the areas of masked and unmasked locks. The photoprotective contribution of the treatment is evaluated relative to an untreated dyed lock that has undergone the same exposure to UV/visible light.

Spectrocolorimetric monitoring accompanies these evaluations. The measurements are taken using a Minolta CM 2022 spectrocolorimeter, before and after exposure to UV/visible light.

The degradation caused by the UV/visible light radiation is expressed as $\Delta E$: $\Delta E$ (exposed area−unexposed area)= $\sqrt{(\Delta L^{*2}+\Delta a^{*2}+\Delta b^{*2})}$.

Results:

It is observed that, after exposure to UV/visible light, the locks that have been subjected to the protective treatment remain much truer to their original color (blue), compared with the untreated locks.

As a result, the treatment process of the invention makes it possible to provide protection with respect to UV/visible radiation, which is markedly higher than for the treated locks without a heating iron.

| Conditions | Measured Areas | Degradation by UV/visible light ΔE (exposed area − unexposed area) | Protection Gain in ΔE relative to the untreated locks |
|---|---|---|---|
| Without Treatment | Unexposed Exposed | 7.75 | — |
| Treatment of the Invention | Unexposed Exposed | 5.75 | 2 |

Example 2

A panel of 10 individuals evaluates the effects of the treatment on dyed hair compared with dyed hair that has not undergone treatment:
1) color fastness after washing with shampoo,
2) color fastness after exposure to UV/visible light,
3) color fastness after washing with shampoo and exposure to light.

Dyeing Step:
Locks of permanent-waved hair containing 90% white hairs are dyed with the shade Majirel 6.1 by mixing the dye product with aqueous hydrogen peroxide solution (L'Oréal professional 20-volumes 6% solution) in a dye product/oxidizing agent ratio of 1 g per 1.5 g and by applying the mixture to the locks. The leave-on time is 15 minutes on each side of the lock. Dyeing is then stopped by rinsing with water.

Protective Treatment Steps:
Composition 2 as described in Example 1 is applied at a rate of 2 g/g of hair. It is then left on for 10 minutes, after which a heating smoothing iron at a temperature of 100° C. is applied by sliding along the fibers.

Shampoo-Fastness and/or UV/Visible Light-Fastness Steps:
The treated locks undergo exposure to UV/visible light and/or six shampoo washes with DOP camomile shampoo.

Results:
The 10 individuals of the panel unanimously indicated that the dyed locks which had undergone the protective treatment of the invention showed, relative to the untreated dyed locks:
(1) better resistance of the original color with respect to shampooing,
(2) better resistance of the original color with respect to light,
(3) better color fastness after washing with shampoo and exposure to light.

Example 3

A panel of 10 individuals evaluates the effects of the treatment on dyed hair with different UV-screening agents having different log (P) values (calculated using the Epiwin software) indicated in the table below, relative to dyed hair that has not undergone treatment:

| iv. Test screening agent | log P |
|---|---|
| Benzophenone-4 (Uvinul MS 40 from BASF) | 0.37 |
| Octocrylene (Uvinul N539 from BASF) | 6.4 |
| Octyl triazone (Uvinul T150 from BASF) | 8.1 |

Dyeing Step:
The dyeing step is identical to that of Example 1.

Protective Treatment Steps:
The protective treatments are performed on dyed locks by applying the compositions indicated in the table below at a rate of 2 g/g of hair:

| v. Ingredients | Composition 1 | Composition 2 | Composition 3 |
|---|---|---|---|
| Ethanol | 20 g | 20 g | 20 g |
| Benzyl alcohol | 10 g | 10 g | 10 g |
| Benzoic acid | 0.5 g | 0.5 g | 0.5 g |
| Benzophenone-4 | 5 g | | |
| Octocrylene | | 5 g | |
| Octyl triazone | | | 5 g |
| Hydroxyethyl oleyl dimonium chloride | 5 g | 5 g | 5 g |
| Water | qs 100 g | qs 100 g | qs 100 g |

The composition is left on for 10 minutes and a heating smoothing iron at a temperature of 100° C. is then applied by sliding along the fibers. The locks are then washed with DOP camomile shampoo and dried.

UV/Visible Light Exposure Steps:
The exposure to UV/visible light is performed under the same conditions as in Example 1.

Results:
The 10 individuals of the panel unanimously indicated that, after exposure to UV/visible light, only the dyed locks that had undergone the treatment with composition 1 containing Benzophenone-4 (log P=6) showed better resistance of the color compared with untreated dyed locks exposed under the same conditions.

The 10 individuals of the panel did not observe any improvement in the resistance of the color with compositions 2 and 3 containing a UV-screening agent with a log P of greater than 6, compared with untreated dyed locks exposed under the same conditions.

Each patent, patent application, publication, text and literature article/report cited or indicated herein is hereby expressly incorporated by reference.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the treatment and protection of human hair artificially dyed by oxidation dyeing, comprising topically applying thereon a composition which comprises, formulated into a physiologically acceptable medium, protective agent selected from the group consisting of benzophenone-1, benzophenone-2 and Ethylhexyl methoxycinnamate, and then heating said treated hair with a heating iron at a temperature of greater than or equal to 60°.

2. The process as defined by claim 1, in which the temperature of the heating iron ranges from 60° C. to 220° C.

3. The process as defined by claim 2, in which the temperature of the heating iron ranges from 60° C. to 120° C.

4. The process as defined by claim 1, in which the iron is applied by successive separate touches of a few seconds, or by gradually moving or sliding along the treated keratin fibers.

5. The process as defined by claim 1, in which a time delay exists between the application of the composition containing the protective agent and contacting the keratin fibers with the heating iron.

6. The process as defined by claim 5, in which the time delay ranges from 30 seconds to 60 minutes.

7. The process as defined by claim 1, comprising a rinsing step and/or a step of washing the keratin fibers with shampoo before or after applying the composition containing the protective agent and optionally after heating with the iron.

8. The process as defined by claim 1, comprising an additional step of total or partial drying of the keratin fibers before heating with the iron.

9. The process as defined by claim 1, in which the protective agents are selected from the group consisting of:
Ethylhexyl methoxycinnamate.

10. The process as defined by claim 1, in which the keratin fiber protective agent(s) has (have) a log P of less than 4.5.

11. The process as defined by claim 1, in which the protective agent(s) is (are) soluble to at least 0.5% in water or $C_1$-$C_4$ lower alcohols at 25° C.

12. The process as defined by claim 1, in which the protective agent(s) is (are) water-soluble organic UV-screening agents.

13. The process as defined by claim 1, in which the keratin fiber protective agent(s) represent(s) from 0.15% to 50% by weight, relative to the total weight of the composition.

14. The process as defined by claim 1, in which the physiologically acceptable medium comprises water or of a mixture of water and of at least one cosmetically acceptable organic solvent.

15. The process as defined by claim 14, in which the medium comprises organic solvents selected from the group consisting of $C_1$-$C_4$ lower alkanols; polyols and polyol ethers, and mixtures thereof.

16. The process as defined by claim 1, in which the composition comprises one or more additives selected from the group consisting of anionic, cationic, nonionic, amphoteric and zwitterionic surfactants or mixtures thereof, anionic, cationic, nonionic, amphoteric or zwitterionic polymers or mixtures thereof, mineral or organic thickeners, anionic, cationic, nonionic and amphoteric polymeric associative thickeners, penetrants, sequestrants, fragrances, buffers, dispersants, conditioning agents, volatile or non-volatile, modified or unmodified silicones, film-forming agents, ceramides, preservatives and opacifiers.

17. The process as defined by claim 1, in which the composition comprises at least one aromatic alcohol and at least one aromatic carboxylic acid.

18. The process as defined by claim 17, in which the aromatic alcohol(s) represent(s) from 0.01% to 50% by weight, relative to the total weight of the composition.

19. The process as defined by claim 18, in which the aromatic alcohol(s) is (are) present in concentrations of greater than 1% by weight.

20. The process as defined by claim 17, in which the aromatic alcohol is benzyl alcohol.

21. The process as defined by claim 17, in which the aromatic acid(s) or salts thereof represent(s) from 0.001% to 30% by weight, relative to the total weight of the composition.

22. The process as defined by claim 17, in which the aromatic acid is benzoic acid.

23. The process as defined by claim 1, in which the composition also comprises at least one conditioning agent.

24. The process as defined by claim 23, in which the conditioning agent(s) represent(s) from 0.001% to 20% by weight, relative to the total weight of the composition.

25. The process as defined by claim 1, in which the composition is in the form of an aqueous or aqueous-alcoholic lotion, a gel, a milk, a cream, an emulsion or a mousse.

26. The process as defined by claim 1, in which the composition is packaged in the form of a vaporizer, a pump-dispenser bottle or in an aerosol container.

27. The process as defined by claim 1, in which the pH of the composition applied to the keratin fibers ranges from 1 to 11.

* * * * *